(12) United States Patent
Sabbadini et al.

(10) Patent No.: US 7,195,759 B2
(45) Date of Patent: Mar. 27, 2007

(54) THERAPEUTIC USES OF GLANDULAR KALLIKREIN

(75) Inventors: Edris Sabbadini, Manitoba (CA); Eva Nagy, Manitoba (CA); Istvan Berczi, Manitoba (CA)

(73) Assignee: The University of Manitoba, Winnipeg (CA)

( * ) Notice: Subject to any disclaimer, the term of this patent is extended or adjusted under 35 U.S.C. 154(b) by 0 days.

(21) Appl. No.: 10/162,697

(22) Filed: Jun. 6, 2002

(65) Prior Publication Data

US 2003/0216306 A1     Nov. 20, 2003

Related U.S. Application Data

(60) Provisional application No. 60/296,153, filed on Jun. 7, 2001.

(30) Foreign Application Priority Data

Jun. 6, 2001    (CA) ................................. 2349748

(51) Int. Cl.
*A61K 38/48* (2006.01)
*C12N 9/48* (2006.01)
*C12N 9/50* (2006.01)

(52) U.S. Cl. .................... 424/94.64; 435/212; 435/219; 514/825

(58) Field of Classification Search ............. 424/94.64, 424/94.1; 435/226, 183
See application file for complete search history.

(56) References Cited

U.S. PATENT DOCUMENTS 5,744,487 A * 4/1998 Ohshima et al. ............ 514/326

OTHER PUBLICATIONS

Croxatto, H.R., et al., 1979. Inhibition of urinary kallikrein excretion by semi-purified renin in the rat. Clinical Science 57: 243s-245s.*
Wikipedia entry: "Kidney." Accessed Jan. 31, 2005. http://www.wikipedia.org/wiki/kidney.*
Catalog listing for anti-rat renin avaliable from Swant, Inc. Accessed Jan. 31, 2005. http://www.swant.com/Antibodies_renin.htm.*
Faria AMC et al. 2005. Oral tolerance. Immunol Rev 206: 232-259.*

* cited by examiner

*Primary Examiner*—Sandra E. Saucier
*Assistant Examiner*—Lora E Barnhart
(74) *Attorney, Agent, or Firm*—Merchant & Gould P.C.

(57) ABSTRACT

An immunosuppressive peptide of 40 kDa molecular weight, isolated from the submandibular glands (SMG*) of rats, had the capacity to suppress immune reactions upon parenteral administration to rats and mice. The peptide was identified as glandular kallikrein (K1) by partial sequencing and by enzymatic activity.

15 Claims, 10 Drawing Sheets

| Protein | 1 | 5 | 10 | 15 | 20 | 25 |
|---|---|---|---|---|---|---|
| 40 kDa | VVGGYNxEMNSQPWQVAVYYFGEYLx | | | | | |
| Gland. Kallikrein | VVGGYNCEMNSQPWQVAVYYFGEYLC | | | | | |
| KLP-S3 | VVGGYNxETNSQPWQVAVIGTxF x | | | | | |
| Tonin | IVGGYKCEKNSQPWQVAVIN EYLC | | | | | |
| Antigen γ | IVGGYKxEKNSQPWQVAIIN EYLx | | | | | |
| T-kininogenase | IVGGYKCEKNSQPWQVAIIIETEYL | | | | | |
| Proteinase B | IVGGYKCEKNSQPWQVAIIN EYLC | | | | | |
| Proteinase A | VIGGYKCEKNDQPWQVALYSFSKYLC | | | | | |

FIG 6

THERAPEUTIC USES OF GLANDULAR KALLIKREIN

PRIOR APPLICATION

This application claims priority under 35 USC § 119(e) to U.S. Ser. No. 60/296,153, filed Jun. 7, 2001.

BACKGROUND OF THE INVENTION

Kallikreins belong to a family of serine proteases capable of cleaving various substrates and generating biologically active peptides. In spite of the names, tissue or glandular kallikreins should be distinguished from plasma kallikrein. They differ from plasma kallikrein in their genes of origin, molecular weight, amino acid sequences, substrates, peptide products and most probably physiological functions. There are at least 20 genes for tissue kallikrein in rodents (98), while in humans 15 genes have been so far described (Yousef, G. M., Scorilas, A., Jung, K., Ashworth, L. K., Diamondis, E. P. J. Biol. Chem. 2001, 276:53–61; Clements, J., Hooper, J., Dong, Y., Harvey, T. Biol. Chem. 2001, 382:5–14). Of these, only one gene in each species codes for true glandular kallikrein. Of the rat genes at least 6–7 appear to be expressed in the submandibular (SM) gland (99). These include true glandular kallikrein, tonin, α and γ nerve growth factor (NGF), and the epidermal growth factor (EGF)-binding protein (EGF-BP), type A, B, and C. As used herein, the term "glandular kallikrein (GK)" refers to true GK, while the general term "kallikrein(s)" (K), will be used for any unspecified members of the tissue kallikrein family. True GK has been designated in various species as kallikrein −1 (K1) (100).

The best known substrates for GK-action are hepatic-derived kininogens (100) which occur in two forms: low molecular weight kininogen (50 kDa) and high molecular weight kininogen (120 kDa). From the action of plasma kallikrein on high molecular weight kininogen a nonapeptide, bradikinin, is generated, while in most species GK gives rise to a decapeptide, kallidin (lys-bradikinin) from either low or high molecular weight kininogen. Kallidin is biologically active in itself but may also be further processed into bradikinin. An exception may be the GK of the rat SMG which was reported to produce bradikinin (101).

While the action of GK on kininogen is particularly well studied, the full range of GK substrates has not yet been investigated. Since GK is, and most of the times remains, localized in certain tissues, physiological substrates are likely to vary from tissue to tissue. Of particular interest here is the possibility that GK may activate or in any way regulate some other immunologically active factors of the SM gland, including NGF, EGF/transforming growth factor (TGF)-α and TGFβ. Thus, salivary gland GK may exert its immunological effects either via the production of classical kinins; or via other immunologically active factors. Moreover, salivary GK is actively secreted in saliva (102) and would be expected to reach various points in the gastrointestinal tract and act on various substrates there.

SUMMARY OF THE INVENTION

According to a first aspect of the invention, there is provided a pharmaceutical composition comprising glandular kallikrein or a bioactive fragment thereof and an antigen.

The antigen may be an auto-antigen. The auto-antigen may be from an autoimmune disease selected from the group consisting of: rheumatoid arthritis, lupus erythrematosis, multiple sclerosis, inflammatory bowel diseases, for example, Crohn's disease and ulcerative colitis, autoimmune hemolytic anemia, autoimmune thrombocytopenic purpura, autoimmune hepatitis and pancreatitis, Goodpasture's syndrome, acute rheumatic fever, pemphigus vulgaris, myasthenia gravis, ankylosing spondylitis, acute anterior uveitis, Grave's disease, Hashimoto's thyroiditis and juvenile diabetes.

The antigen may be a gene therapy vector.

According to a second aspect of the invention, there is provided a method of inducing tolerance to at least one orally administered antigen in an animal comprising administering to said animal an effective amount of a glandular kallikrein or a bioactive fragment thereof.

The amount administered may be sufficient to reduce the animal's immune response to the antigen.

The method may include co-administering an antigen with the glandular kallikrein.

The antigen may be from an autoimmune disease selected from the group consisting of: rheumatoid arthritis, lupus erythrematosis, multiple sclerosis, inflammatory bowel diseases, for example, Crohn's disease and ulcerative colitis, autoimmune hemolytic anemia, autoimmune thrombocytopenic purpura, autoimmune hepatitis and pancreatitis, Goodpasture's syndrome, acute rheumatic fever, pemphigus vulgaris, myasthenia gravis, ankylosing spondylitis, acute anterior uveitis, Grave's disease, Hashimoto's thyroiditis and juvenile diabetes.

According to a third aspect of the invention, there is provided a method of ameliorating symptoms associated with an autoimmune disorder in an animal afflicted with said autoimmune disorder comprising administering to said animal an effective amount of a glandular kallikrein or a bioactive fragment thereof.

The method may include co-administering an antigen with the glandular kallikrein.

The autoimmune disease may be selected from the group consisting of: rheumatoid arthritis, lupus erythrematosis, multiple sclerosis, inflammatory bowel diseases, for example, Crohn's disease and ulcerative colitis, autoimmune hemolytic anemia, autoimmune thrombocytopenic purpura, autoimmune hepatitis and pancreatitis, Goodpasture's syndrome, acute rheumatic fever, pemphigus vulgaris, myasthenia gravis, ankylosing spondylitis, acute anterior uveitis, Grave's disease, Hashimoto's thyroiditis and juvenile diabetes.

According to a fourth aspect of the invention, there is provided a method of enhancing an immune response to at least one orally administered antigen comprising administering to said animal an effective amount of a glandular kallikrein inhibitor.

The amount administered may be sufficient to reduce the animal's tolerance to the antigen.

The method may include co-administering an antigen with the glandular kallikrein inhibitor.

The antigen may be an oral vaccine.

μg/animal; corresponding to the yield from one SMG) in 0.2 ml of PBS. Controls received PBS alone. On day 6 the mice were challenged by the application of 0.1% solution of picryl chloride in olive oil to both sides of the ear. The thickness of the ear was measured 24 hrs after challenge and the results were compared with that of controls. The results are expressed in units of 1/10 mm. The bars represent the mean increase of thickness ± SE. of the challenged ear. Unimmunized controls did not show any increase in ear thickness (not shown).

Figure 2A:
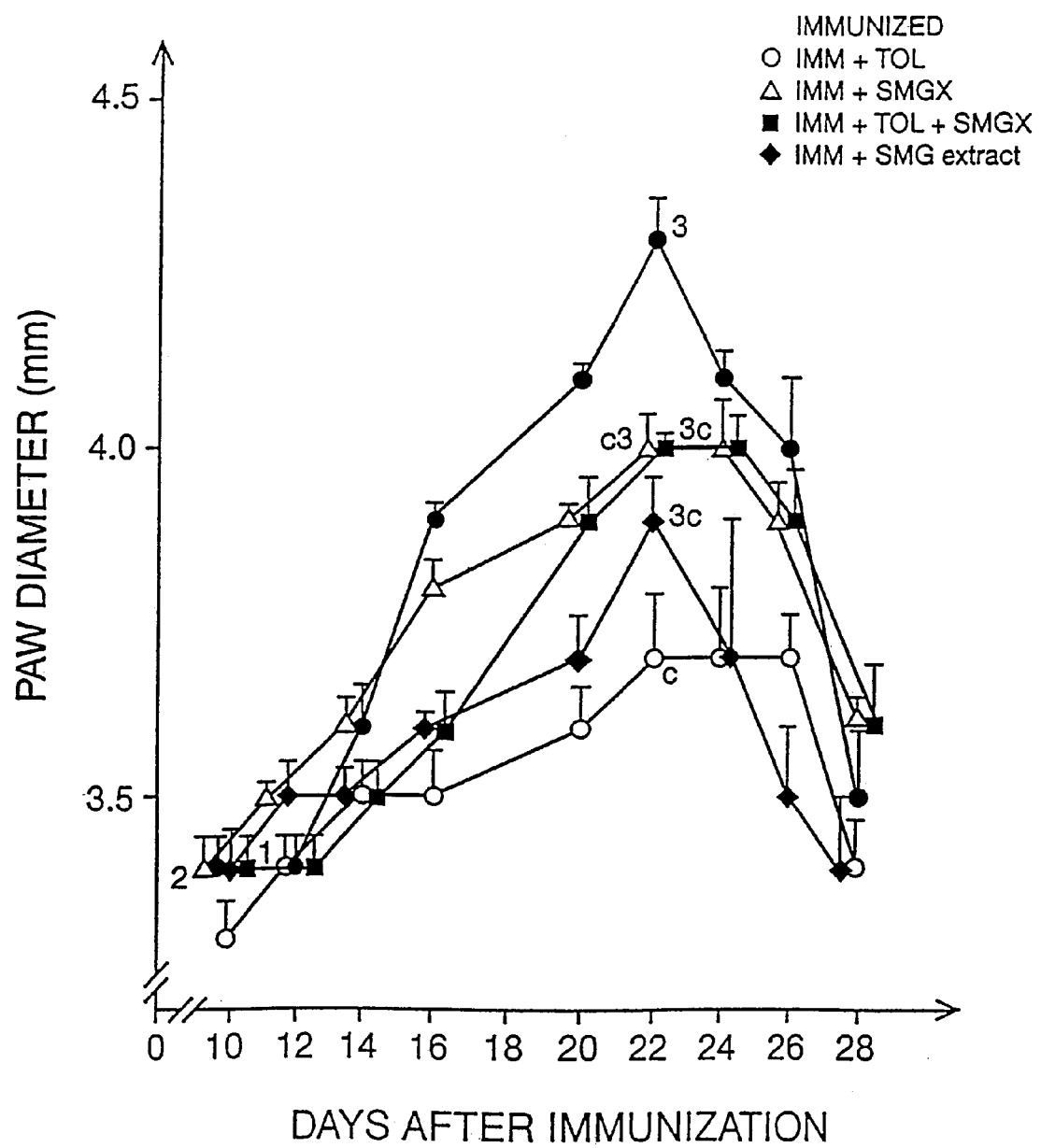

FIG. 2A shows the effect of SMGx and rK1 on CA and on the induction of oral tolerance in Sprague Dawley rats. Compared to control: a) $p<0.05$ b) $p<0.01$ c) $p<0.001$ Compared to tolerized group: 1) $p<0.05$ 2) $p<0.01$ 3) $p<0.001$ Groups of 4 male Sprague-Dawley rats were used, weighing 200–300 g. SMGx was performed on day −21, treatment with native bovine type II collagen was done with 3 μg of daily dose by gavage on days −7, −5 and −2. Immunization was done with 75 μg of BCII in incomplete Freund's adjuvant, injected i.d. at the base of the tail on days 0 and on 7. Semipurified rK1 (GK) was given s.c. in doses equivalent to 50% of the yield from one SMG rat on days 16,18 and 20.

Figure 2B:
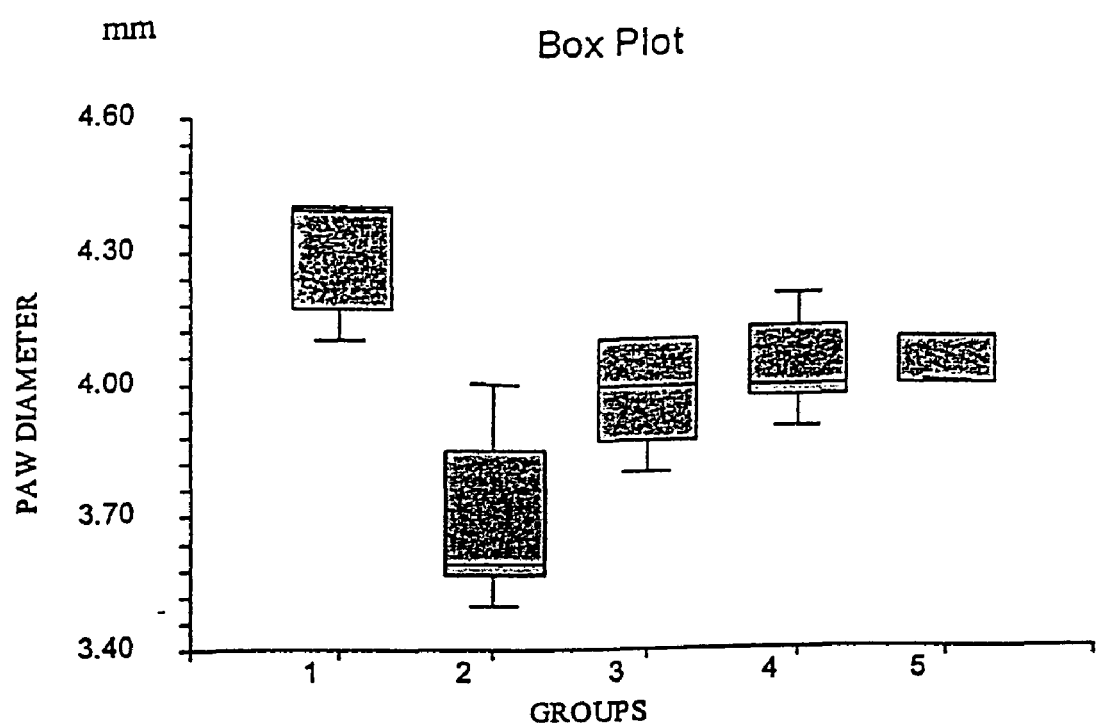

FIG. 2B—Analysis of variance report, day 22. Bonferroni (with control) multiple-comparison test Response: 1, 2, 3, 4, 5

Term A:

| Group | Count | Mean | Different from groups |
|---|---|---|---|
| Alpha = 0.050 Error term = S(A) DF = 45 MSE = 1.653333E-02 Critical Value = 2.602083 | | | |
| 2 lmm + Tol | 10 | 3.7 | 3,4,5,1 |
| 3 lmm + SMGx | 10 | 3.98 | 2,1 |
| 4 lmm + Tol + SMGx | 10 | 4.04 | 2,1 |
| 5 lmm + SMGextract | 10 | 4.04 | 2,1 |
| 1 Immunized | 10 | 4.3 | 2,3,4,5 |
| Alpha = 0.010 Error Term = S(A) DF = 45 MSE = 1.653333E-02 Critical value 3.202842 | | | |
| 2 lmm + Tol | 10 | 3.7 | 3,4,5,1 |
| 3 lmm + SMGx | 10 | 3.98 | 2,1 |
| 4 lmm + Tol + SMGx | 10 | 4.04 | 2,1 |
| 5 lmm + SMGextract | 10 | 4.04 | 2,1 |
| 1 Immunized | 10 | 4.3 | 2,3,4,5 |
| Alpha = 0.001 Error Term = S(A) DF = 45 MSE = 1.653333E-02 Critical Value 3.977715 | | | |
| 2 lmm + Tol | 10 | 3.7 | 3,4,5,1 |
| 3 lmm + SMGx | 10 | 3.98 | 2,1 |
| 4 lmm + Tol + SMGx | 10 | 4.04 | 2,1 |
| 5 lmm + SMGextract | 10 | 4.04 | 2,1 |
| 1 Immunized | 10 | 4.3 | 2,3,4,5 |

Figure 3A:
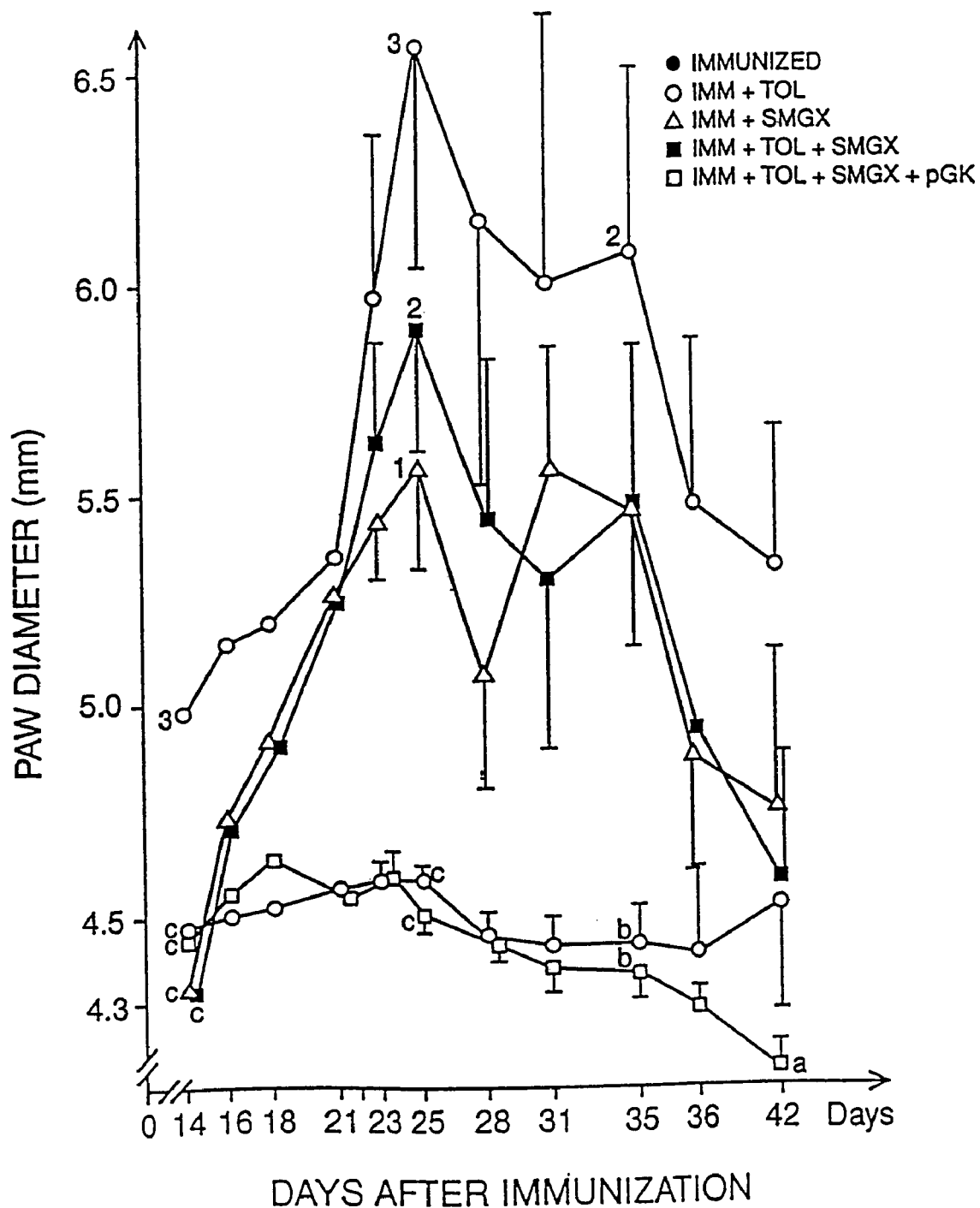

FIG. 3A shows that salivary K1 is required for the induction of oral tolerance against CA in Lewis rats. Compared to control: a) $p<0.05$ b) $p<0.01$ c) $p<0.001$ Compared to tolerized group: 1) $p<0.05$ 2) $p<0.01$ 3) $p<0.001$ Groups of 5 female Lewis rats were used. SMGx was performed on day −21. Kallikrein was given at doses of 100 IU/0.5 ml/rat by gavage on days −8, −5, −3. Native bovine collagen type II (Sigma) was given orally at doses of 3 μg/rat in 0.5 ml distilled water on days −7, −5, −3 (39). Immunization was done on days 0 and day 7 with BCII dissolved in 1 mM acetic acid (at 1.5 mg/ml) and emulsified with an equal volume of incomplete Freund's adjuvant. Each rat received 0.1 ml of antigen (containing 75 μg BCII) injected interdermally at the base of the tail (8). The diameters of the hind paws were measured, and plotted in the figure as mean ± SE.

Figure 3B:
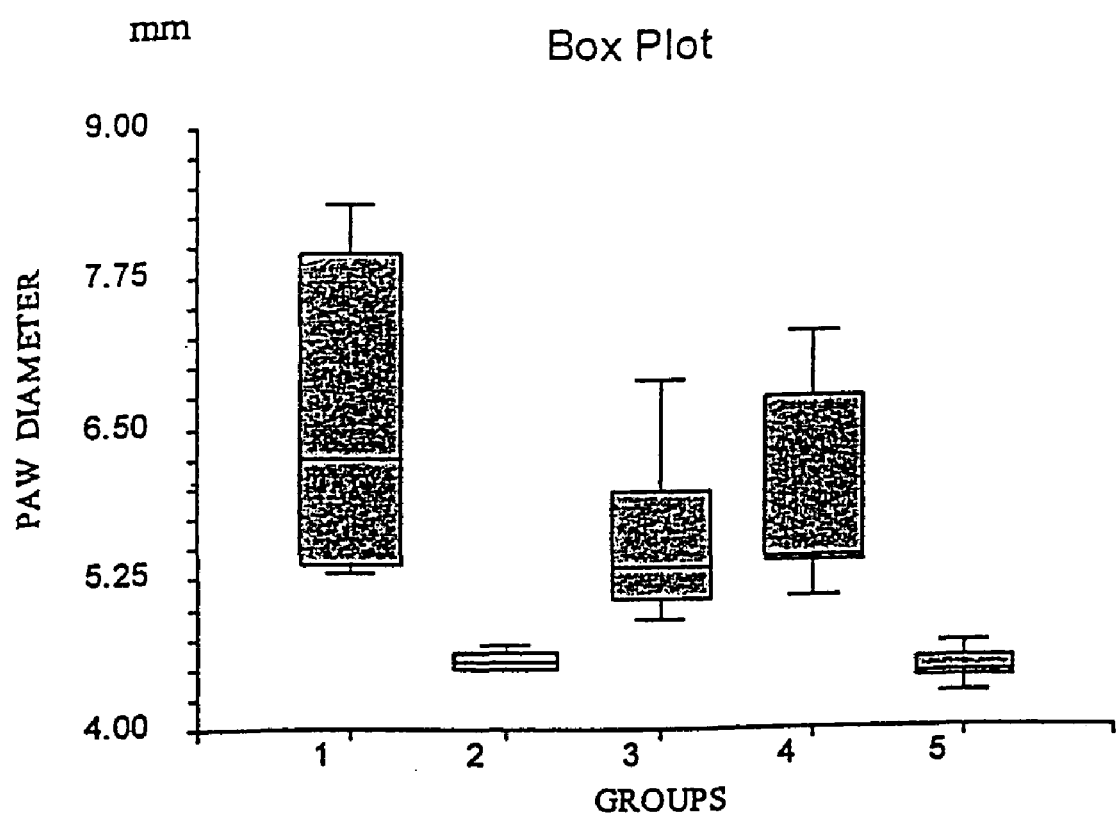

FIG. 3B. Analysis of variance report, day 25 Bonferroni (with control) multiple-comparison test Response: 1, 2, 3, 4, 5

Term A:

| Group | Count | Mean | Different from groups |
|---|---|---|---|
| Alpha = 0.050 Error term = S(A) DF = 33 MSE = 0.5016446 Critical Value = 2.642069 | | | |
| 5 Imm, Tol SmGx, pGK | 8 | 4.5 | 3, 4, 1 |
| 2 Imm + Tot | 8 | 4.575 | 3, 4, 1 |
| 3 Imm + SMGx | 8 | 5.55625 | 5, 2 |
| 4 Imm + Tol + SMGx | 8 | 5.8875 | 5, 2 |
| 1 Immunized | 8 | 6.566667 | 5, 2 |
| Alpha = 0.010 Error Term = S(A) DF = 33 MSE = 0.5016446 Critical value 3.272916 | | | |
| 5 Imm, Tol SmGx, pGK | 8 | 4.5 | 4, 1 |
| 2 Imm + Tol | 8 | 4.575 | 4, 1 |
| 3 Imm + SMGx | 8 | 5.55625 | |
| 4 Imm + Tol + SMGx | 8 | 5.8875 | 5, 2 |
| 1 Immunized | 8 | 6.566667 | 5, 2 |
| Alpha = 0.001 Error Term = S(A) DF = 45 MSE = 1.653333E-02 Critical Value 3.977715 | | | |
| 5 Imm, Tol SmGx, pGK | 8 | 4.5 | 1 |
| 2 Imm + Tol | 8 | 4.575 | 1 |
| 3 Imm + SMGx | 8 | 5.55625 | |
| 4 Imm + Tol + SMGx | 8 | 5.8875 | |
| 1 Immunized | 8 | 6.566667 | 5, 2 |

Figure 4:
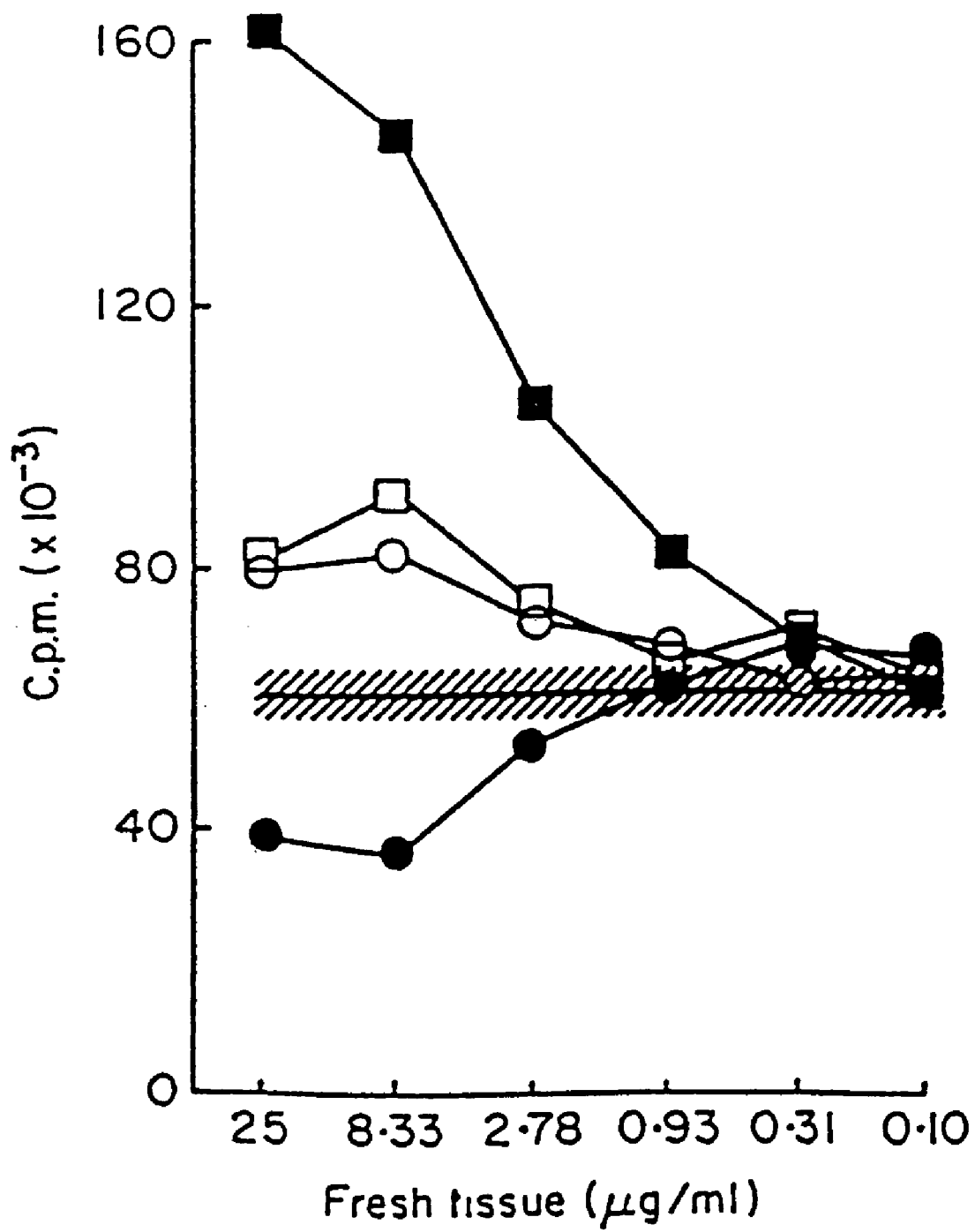

FIG. 4 shows the effects of pooled Sephacryl fractions of submandibular and parotid glands on the Con A stimulated lymph node cell proliferation. The effects of pooled Sephacryl fractions of submandibular (●,■) and parotid (○,□) glands on the Con A stimulated lymph node cell proliferation: (●,○) MW>50 kDa; (●,□) MW<50 kDa. The solid horizontal line is the value of mean c.p.m. for the controls and the shaded area represents the 95% confidence limits. From Ref. 12.

Figure 5:
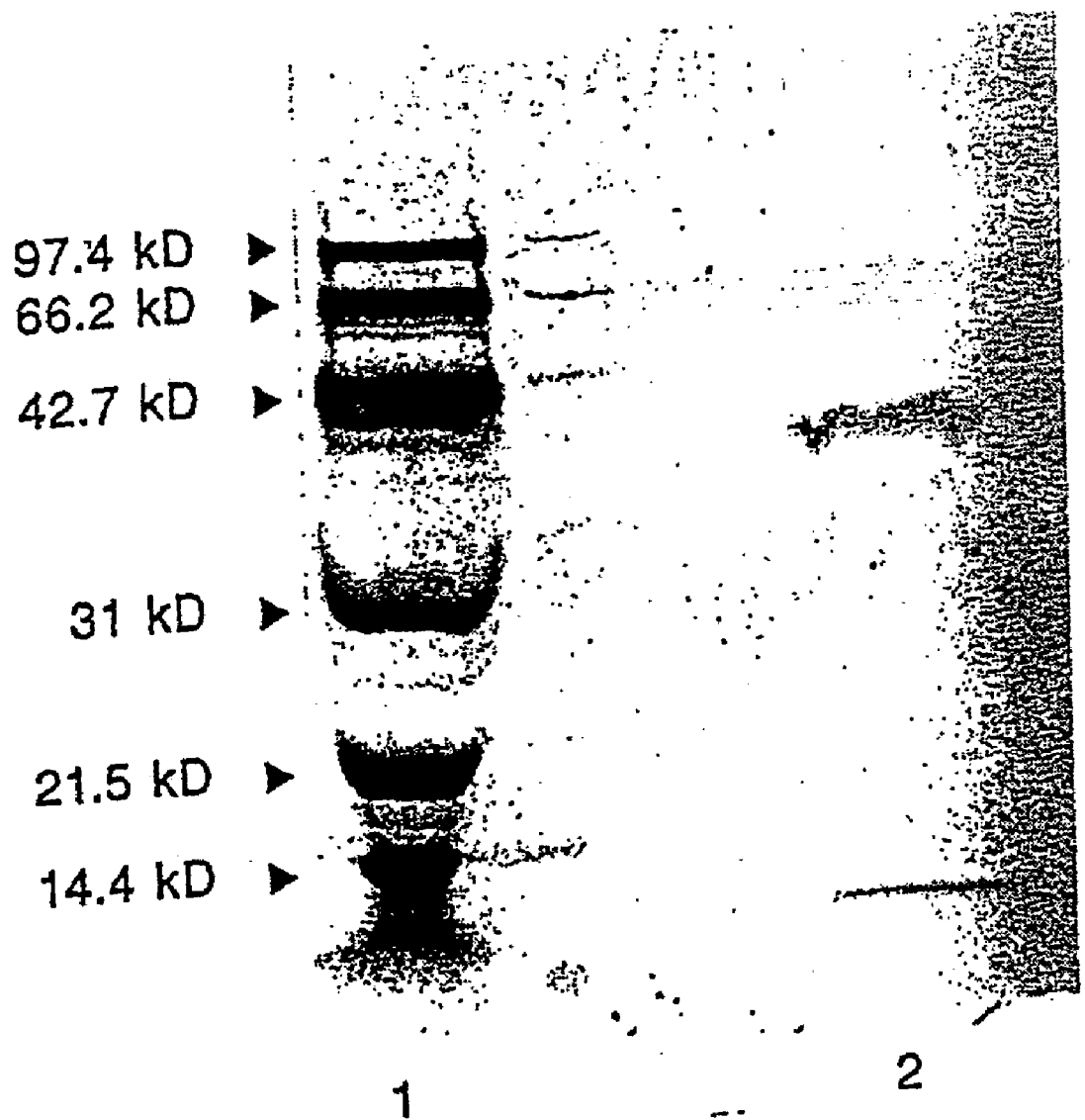

FIG. 5 is an SDS PAGE of the purified protein from rat SM gland (lane 2). Molecular weight standards are shown in lane 1. From Ref. 14.

FIG. 6 is a partial N-terminal amino acid sequence of the 40 kDa protein (SEQ ID No. 1) isolated from rat SM gland compared with those of members of kallikrein family expressed in the rat SM gland. The boxed areas represent regions of identity with the 40 kDa protein. Blank spaces are used to align homologous sequences in different proteins. x=not identified. From Ref. 14.

Figure 7:
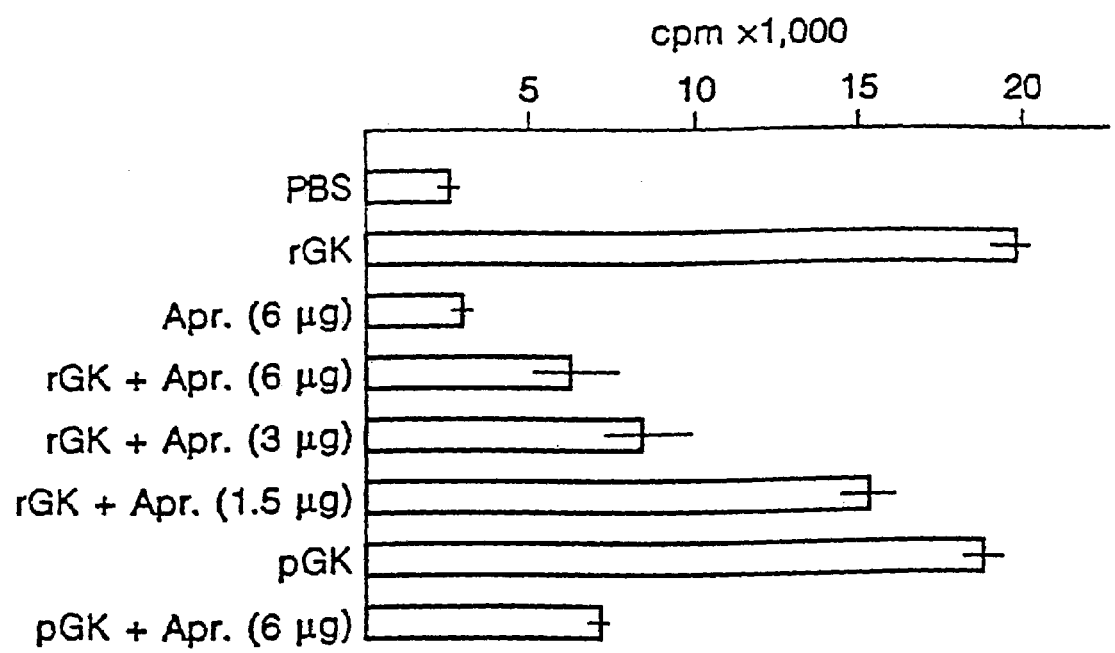

FIG. 7 shows increased proliferative activity of Con A stimulated A/J lymph node cells induced by rGK and pGK and reversal of this effect with aprotinin. The rGK and pGK doses were 1.78 μg/culture (final concentration 0.22 μM/l). Aprotinin (Apr.) doses were: 6 μg, 3 μg, or 1.5 μg per culture 4.6 μM/l, 2.3 μM/l, and 1.15 μM/l, respectively). Results are expressed as counts per minute (C.P.M.) in triplicate cultures (S.D.). From Ref. 14.

Figure 8:
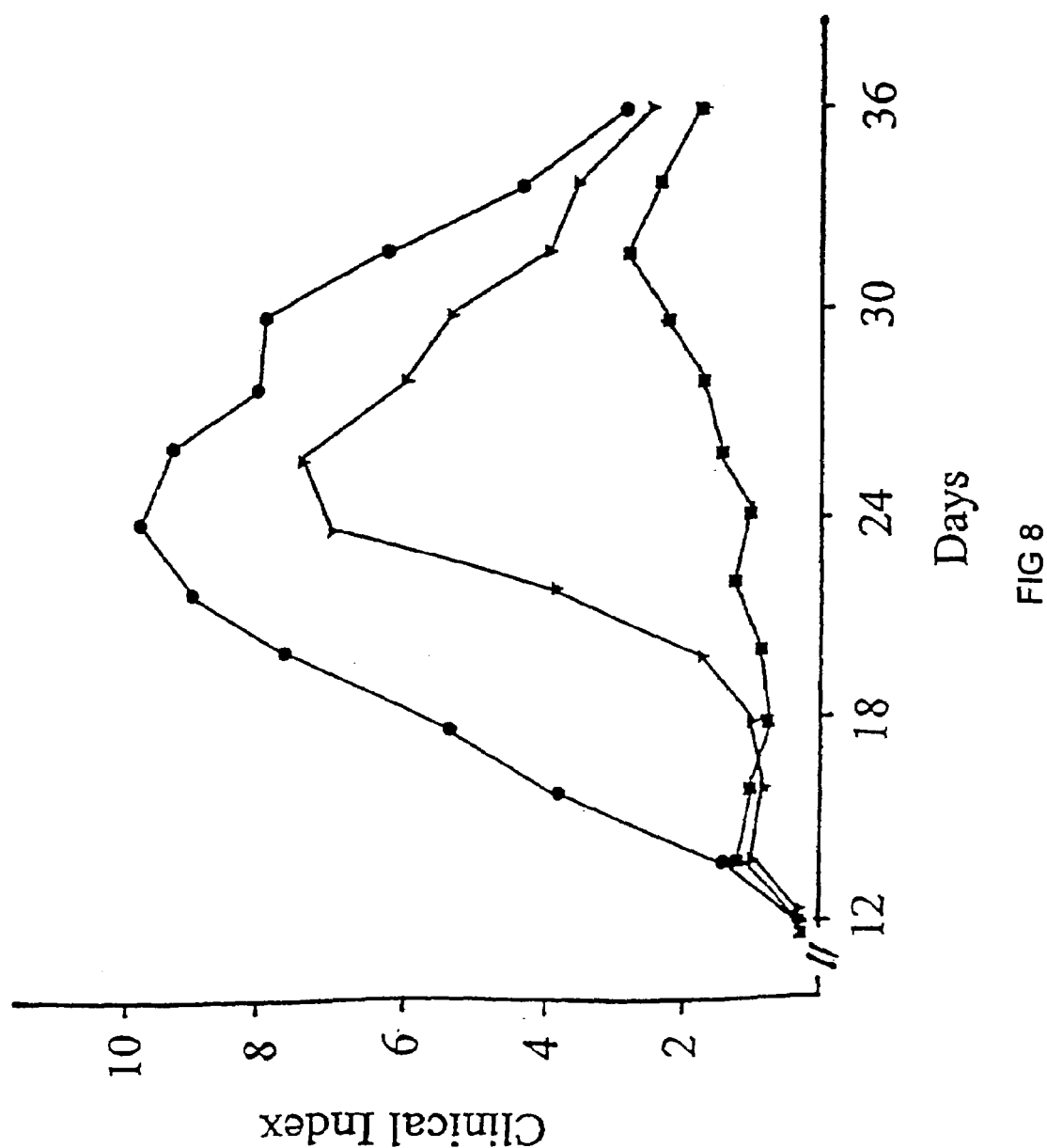

FIG. 8 shows the effects of single or multiple injections of a semi-purified preparation of rGK in the CA model. Effects of a single (▼, day 14) or multiple (■, days 14, 18 and 24) injections of a semi-purified preparation of rGK in the CA model. Controls (●) received PBS only.

TABLE 1 shows functional disability in rats with arthritis.

TABLE 2 shows effects of high molecular weight (HMW) and low molecular (LMVV) pools of gel filtration fractions in three in viva immunological assays.

TABLE 3 shows effects of the intradermal injection of rGK given before or after immunization in the DTH model.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "effective amount" refers to the administration of an amount of a given compound that achieves the desired effect.

As used herein, "purified" does not require absolute purity but is instead intended as a relative definition. For example, purification of starting material or natural material to at least one order of magnitude, preferably two or three orders of magnitude is expressly contemplated as falling within the definition of "purified".

As used herein, "glandular kallikrein" refers to the enzymes described in different mammalian species by several authors (Richards, R. I., Catanzaro, D. F., Mason, A. J., Morris, B. J., Baxter, J. D., Shine, J., J. Biol. Chem. 1982, 257:2758–61; James, M. N., Delbaere, L. T., Brayer, G. D., Can. J. Biochem. 1978, 396–402; Fiedler, F. Lemon, M. J., Hirschauer, C., Leysath, G., Lottspech, F., Henschen, A., Gau, W., Bhoola, K. D., Biochem. J. 1983, 125–34; Swift, G. H., Dagorn, J. C., Ashley, P. L., Cummings, S. W., MacDonald, R. J., Proc. Nat. Acad. Sci. U.S.A., 1982, 79: 7263–7; Tschetsche, H., Mair, G., Godec, G., Adv. Exp. Med. Biol. 1979, 120A:245–60). We are not making any claims here about possible uses of other members of the serine protease family.

As used herein, the term "treating" in its various grammatical forms refers to preventing, curing, reversing, attenuating, alleviating, minimizing, suppressing or halting the deleterious effects of a disease state, disease progression, disease causitive agent or other abnormal condition.

As used herein, "autoimmune disease" refers to diseases wherein the host immune system recognizes "self" material as foreign. Examples include but are by no means limited to rheumatoid arthritis, multiple sclerosis, inflammatory bowel diseases, for example, Crohn's disease and ulcerative colitis, autoimmune hemolytic anemia, autoimmune thrombocytopenic purpura, autoimmune hepatitis and pancreatitis, Goodpasture's syndrome, acute rheumatic fever, pemphigus vulgaris, myasthenia gravis, ankylosing spondylitis, acute anterior uveitis, Grave's disease, Hashimoto's thyroiditis and juvenile diabetes.

As used herein, "antigen" refers to any material potentially recognized by a host immune system as "non-self".

As used herein, "a biologically active fragment" refers to a fragment of the glandular kallikrein, which retains its biological activity, that is, serine protease activity.

As used herein, "animal" refers to vertebrates. It is of note that the patient may be a human.

Described herein is a method of enhancing tolerance in an animal to material recognized by the animal as foreign comprising administering glandular kallikrein either in combination with or prior to host exposure to the foreign material. In some embodiments, the "foreign" material, for example an antigen, and the glandular kallikrein are taken orally. It is of note that the "foreign" material may be for example an auto-antigen.

In some embodiments, the glandular kallikrein, or a bioactive fragment thereof, with or without an antigen may be combined with other compounds or compositions known in the art such that the glandular kallikrein is a pharmaceutical composition in the form of, for example, a pill, tablet, liquid, film or coating using means known in the art and as discussed below.

It is of note that the glandular kallikrein with or without an antigen discussed above may be prepared to be administered in a variety of ways, for example, topically, orally, intravenously, intramuscularly, subcutaneously, intraperitoneally, intranasally or by local or systemic intravascular infusion using means known in the art and as discussed below.

It is of note that as discussed herein, the above-described pharmaceutical composition may be arranged to be delivered in 3-day intervals at an oral dosage of about 10–5000 International Units, or of about 100–1000 IU, or more preferably, 500 International Units (IU) per kg of the subject. This dosage is based on our experience with rats. This in other embodiments, the daily dosage may be about 170 IU/kg of the subject. As will be apparent to one knowledgeable in the art, the total dosage will vary according to the weight, health and circumstances of the individual.

In some embodiments, the above-described pharmaceutical composition at concentrations or dosages discussed above may be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, *Remington: The Science and Practice of Pharmacy*, 1995, Gennaro ed.

As will be apparent to one knowledgeable in the art, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

In other embodiments, the above-described pharmaceutical composition at concentrations or dosages described above may be encapsulated for delivery. Specifically, the pharmaceutical composition may be encapsulated in biodegradable microspheres, microcapsules, microparticles, or nanospheres. The delivery vehicles may be composed of, for example, hyaluronic acid, polyethylene glycol, poly(lactic acid), gelatin, poly(E-caprolactone), or a poly(lactic-glycolic) acid polymer. Combinations may also be used, as, for example, gelatin nanospheres may be coated with a polymer of poly(lactic-glycolic) acid. As will be apparent to one knowledgeable in the art, these and other suitable delivery vehicles may be prepared according to protocols known in the art and utilized for delivery of the glandular kallikrein. Alternatively, the delivery vehicle may be suspended in saline and used as a nanospray for aerosol dispersion onto an area of interest. Furthermore, the delivery vehicle may be dispersed in a gel or paste, thereby forming a nanopaste for coating a tissue or tissue portion.

It is of note that the glandular kallikrein compositions as described above may be combined with permeation enhancers known in the art for improving delivery. Examples of permeation enhancers include, but are by no means limited to those compounds described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011, 949; and Idson, 1975, J. Pharm. Sci. 64:901–924.

In some embodiments, the pharmaceutical composition in any suitable form as described above, may be combined with biological or synthetic targetting molecules, for example, site-specific binding proteins, antibodies, lectins or ligands, for targetting the glandular kallikrein to a specific region or location.

Described below are sample treatments for exemplary autoimmune and hyper-sensitive disorders for illustrative purposes. As will be apparent to one of skill in the art, the treatment methods may be applied to any suitable disease or disorder. It is further of note that antigens implicated in many autoimmune disorders are well known in the art.

As discussed above, multiple sclerosis is a chronic neurological disorder that affects the nervous system and is believed to be an autoimmune disorder. Specifically, cell migration of a macrophage-like activity is involved in the destruction of the myelin. As discussed above, administration of glandular kallikrein or a bioactive fragment thereof combined with antigen(s) related to multiple sclerosis or possibly the myelin itself would induce tolerance of these compounds, thereby inhibiting demyelination by the patient's immune system, thereby reducing severity of the disease. That is, the glandular kallikrein composition would accomplish at least the following: decrease the severity of symptoms, decrease the duration of disease exacerbations, increase the frequency and duration of disease remission and/or symptom free periods, prevent or attenuate chronic progression of the disease, improve visual symptoms, improve gait disorders, such as, weakness, axial instability, sensory loss, spasticity, hyperreflexia and/or loss of dexterity, improve cognitive impairment, reduce myelin loss, reduce breakdown of the blood-brain barrier and reduce perivascular infiltration of mononuclear cells. In these embodiments, the glandular kallikrein composition may be ingested as a tablet or pill, applied topically or injected, prepared at appropriate concentrations or dosages as described herein.

Similarly, inflammatory bowel diseases are caused by intestinal inflammation and repeated inflammatory responses. As discussed above, administering glandular kallikrein or a bioactive fragment thereof with antigen(s) implicated in or related to the inflammatory bowel diseases would induce tolerance, thereby reducing the severity of the disease. Specifically, the glandular kallikrein composition would accomplish at least one of the following: decrease the frequency of the attacks, increase the duration of remission periods, decrease the severity or duration of abscess formation, intestinal obstruction, intestinal perforation and the like as well as ameliorate or reduce symptoms such as bloody diarrhea, abdominal pain, fever, weight loss and abdominal distension.

Arthritis is believed to be an autoimmune disease, characterized by infiltration of the joints with inflammatory system cells. As such, administration of glandular kallikrein or a bioactive fragment thereof in combination with antigen(s) related to or implicated in arthritis will induce tolerance to these antigens, thereby inhibiting progression of the autoimmune disease. Specifically, the glandular kallikrein composition will accomplish at least one of the following: decrease severity of symptoms, including pain, swelling and tenderness of affected joints, weakness and fatigue, decrease severity of clinical signs, including thickening of the joint capsule, synovial hypertrophy, decreased range of motion, fixed joint deformity and soft tissue contractures, increase the frequency and duration of remission or disease-free periods and prevent or attenuate chronic progression of the disease. In these embodiments, the glandular kallikrein composition is arranged to be injected directly into the afflicted joints or taken orally. Preparation of the glandular kallikrein composition for injection is described herein.

Glandular kallikrein compositions could also be used to induce oral tolerance against graft rejection and sprayed or applied to tissue grafts or organs prior to transplantation. As discussed above, the glandular kallikreins or bioactive fragments thereof induce tolerance and inhibit the immune response, meaning that prior oral application of the glandular kallikrein compositions would inhibit rejection of the transplanted material. The glandular kallikrein composition will accomplish at least one of the following: prolong the life of the graft; decrease the side effects associated with immunosuppressive therapy and decrease accelerated atherosclerosis associated with transplants. In other embodiments, a mesh coated or arranged to release the glandular kallikrein composition may be used in lieu of spray application.

Juvenile Diabetes or Type I Diabetes is a chronic condition in which the beta cells in the pancreas make little or no insulin because these cells are destroyed by the host immune system. This in turn destroys the islet cells' insulin-producing capacity which in turn brings on diabetes. Thus, the early administration of glandular kallikrein orally or a bioactive fragment thereof, in combination with antigen(s) linked to or implicated in Juvenile Diabetes will accomplish at least one of the following: decrease severity of symptoms, decrease severity of clinical signs, increase time periods between insulin treatments, increase the frequency and duration of remission or disease-free periods and prevent or attenuate chronic progression of the disease.

The invention provides kits for carrying out the methods of the invention. Accordingly, a variety of kits are provided. The kits may be used for any one or more of the following (and, accordingly, may contain instructions for any one or more of the following) uses: treating multiple sclerosis, myasthenia gravis, arthritis, inflammatory bowel diseases, tissue grafts, in an individual; preventing an autoimmune response, inflammation or prolonged inflammatory response in an individual at risk of multiple sclerosis, myasthenia gravis, arthritis, inflammatory bowel diseases, tissue grafts; preventing one or more symptoms of an autoimmune response, swelling, pain, inflammation, prolonged inflammatory response or the like in an individual at risk of multiple sclerosis, myasthenia gravis, arthritis, inflammatory bowel diseases, tissue grafts; reducing severity one or more symptoms of an autoimmune response, swelling, pain, inflammation, or prolonged inflammatory response in an individual; reducing recurrence of one or more symptoms of an autoimmune response, swelling, pain, inflammation, or prolonged inflammatory response in an individual; suppressing an autoimmune response, swelling, pain, inflammation, or prolonged inflammatory response in an individual at risk of multiple sclerosis, myasthenia gravis, arthritis, inflammatory bowel diseases, tissue grafts; delaying development of an autoimmune response, swelling, pain, inflammation, or prolonged inflammatory response and/or a symptom of multiple sclerosis, myasthenia gravis, arthritis, inflammatory bowel diseases, tissue grafts in an individual; and reducing duration of an autoimmune response, swelling, pain, inflammation, or prolonged inflammatory response in an individual.

The kits of the invention comprise one or more containers comprising a glandular kallikrein or a bioactive fragment thereof, a suitable excipient as described herein and a set of instructions, generally written instructions although electronic storage media (e.g., magnetic diskette or optical disk) containing instructions are also acceptable, relating to the use and dosage of the glandular kallikrein for the intended treatment (e.g., multiple sclerosis, myasthenia gravis, arthritis, inflammatory bowel diseases, tissue grafts, or the like). The instructions included with the kit generally include information as to dosage, dosing schedule, and route of administration for the intended treatment. The containers of the glandular kallikrein may be unit doses, bulk packages (e.g., multi-dose packages) or sub-unit doses. As discussed above, antigens for specific autoimmune disorders or allergies may be incorporated into the pharmaceutical composition or may be provided as separate pharmaceutical compositions, prepared as described above. The kit may also include specific antigens for co-administration with the glandular kallikrein or may be incorporated into the pharmaceutical composition.

As discussed above, glandular kallikrein (GK) is an enzyme of the serine protease family capable of generating biologically active peptides by partially degrading various substrates. It is found in several tissues with particularly high concentrations in salivary glands, pancreas, kidney and the prostate gland. The physiological functions of this enzyme appear to vary according to the tissue in which it acts and the substrate(s) available in such tissues.

Several in vitro effects of kallikreins on cells of the immune system have been reported. Thus, several authors have described mitogenic and co-mitogenic effects of kallikrein and other serine proteases. Such mitogenic effects were observed with thymocytes (103), T cells and B cells (104). Although bradikinin may also have mitogenic effects (105), the involvement of this kinin in kallikrein-induced mitogenesis is not well investigated. Moreover, several proteases, including kallikrein, were shown to be involved in immunoglobulin isotype control. Thus Ishizaka described a kallikrein-like factor called glycosylation-enhancing factor, which induced CD4+ T cells to produce an IgE-potentiating factor and to favour the production of IgE by memory B cells (106). Serine proteases from *Schistosoma mansoni* schistosomula were reported to enhance IgE production (107). Moreover, the addition of kallikrein and other serine proteases in various concentrations to cultures of B cells stimulated with LPS and IL 4 enhanced the production of IgE, IgG1, or IgG3, depending on the enzyme concentration used (108).

Our interest in GK arose from studies on immunosuppressive factors in the SM gland of rats. The addition of crude extracts from rat SM glands to murine spleen and lymph node cultures stimulated with concanavalin A (Con A) induced either suppression (at high concentrations) or further stimulation (at lower concentrations) of proliferative activity (109). This suggested that these extracts contained factors with suppressive effects as well as factors with the ability to enhance lymphocyte proliferation. Gel filtration of the crude extracts revealed that the in vitro suppressive activity was due to factors with molecular weight higher than 50 kilo-Daltons (kDa), while stimulation was due to factors with molecular weight lower than 50 kDa (FIG. 4). We tested the in vivo activity of both the higher and lower molecular weight fractions in the skin allograft, direct plaque forming cell response and in the delayed-type hypersensitivity (DTH) models (110). As shown in Table 2, and contrary to what one might have expected in view of their in vitro suppressive activity, the high molecular weight fractions did not have any significant effect in these models. On the other hand, the lower molecular weight fractions produced significant suppression in all three models.

Fractionation of the lower molecular weight pool of fractions through the successive steps of hydrophobic interaction, anion exchange chromatography and a final gel filtration step led to the isolation a single protein (FIG. 5) which retained the properties of in vitro stimulation of lymphocyte proliferation and in vivo immunosuppression (results not shown). The isolated protein was amino acid sequenced (111) using an automated Edman degradation procedure (112). FIG. 6 shows the partial N-terminal amino acid sequence of the 40 kDa protein and of the members of the kallikrein family represented in the rat SMG. The x's (unidentified amino acids) in our sequence are probably cisteins which are destroyed in the Edman degradation process. If this is taken into account, the first 25 amino acids of our protein has identical sequence with that of true GK and differ from those of other members of the kallikrein family. In view of the fact that no other rat proteins with the same amino acid sequence are known, it was concluded that the isolated protein was true rat GK (rGK).

The esterase activity of the isolated rGK was about the same as that of a commercially obtained porcine GK (pGK) when measured in the 2-N-benzoyl-arginine ethyl ester (BAEE) assay (113). Different concentrations of aprotinin induced different degrees of inhibition. FIG. 7 demonstrates the effects of rGK and pGK in the presence or in the absence of aprotinin on the proliferative activity of Con A stimulated murine lymph node cells. The same concentrations of pGK induced similar co-mitogenic effects. Con A concentration in these experiments was such that it induced only suboptimal mitogenic effects, suitable for the demonstration of the co-mitogenic activity of rGK. The addition of different concentrations of aprotinin to the co-stimulated cultures induced dose dependent suppression. It should be noted that the highest concentration of aprotinin used in this experiment (1.5 µg/ml or 6 µg/culture) was capable of inducing about 90% inhibition in the BAEE assay. On the other hand, the lowest concentration of aprotinin (1.5 µg/culture) induced about 40% inhibition of the enzymatic activity and produced partial inhibition of the co-mitogenic activity.

Figure 1:
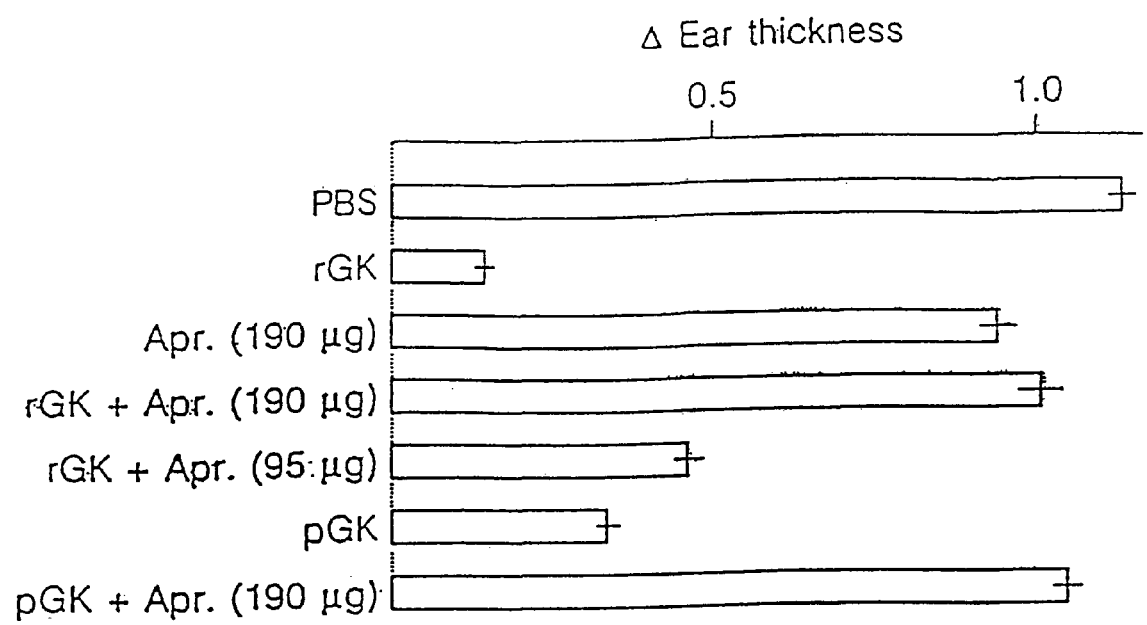
FIG. 1 shows glandular kallikrein inhibition of the effector phase of contact sensitivity in mice. A/J mice were sensitized by application of 0.1 ml of a 5% solution of picryl chloride in ethanol to the clipped skin of the abdomen. On day five after sensitization the mice received aprotinin (Apr.), injected s.c. as a full dose (190 μg/animal) or as a half dose. Fifteen minutes later the animals received a further s.c. injection of rat (r) or pig (p) glandular kallikrein (GK) (57

The results of an in vivo experiment along the same lines are presented in FIG. 1. A DTH reaction was induced in mice sensitized with picryl chloride and challenged with the same agent six days later. The injection of rGK 24 hr before challenge resulted in an almost complete suppression of the response. Similar suppression was obtained with pGK. The dose of rGK used in this experiment (57 μg/animal) was based on our previous experience. The higher of the two aprotinin doses (190 μg/animal) was selected so as to provide, after dilution in the blood stream, a concentration similar to that used in the in vitro experiments. The suppressive effects of rGK and pGK were almost completely removed by the injection of this higher dose of aprotinin given immediately before GK injection. On the other hand, a lower dose of aprotinin induced only partial suppression of the rGK effects. These two experiments clearly demonstrate that the enzymatic activity of GK must be preserved in order to retain its in vivo and in vitro immunological effects.

Table 3 demonstrates the effects of varying the time of GK injection with respect to the time of immunization or of challenge in the DTH model in mice. If given before immunization, GK had a suppressive effect lasting for at least fourteen days. This suggested that the animals did not develop any immunity when presented with the antigen. On the other hand, if GK was given after the development of immunity, it induced a short lived suppression of the skin reaction with a full recovery of reactivity a week after GK administration. This demonstrated that GK did not affect the state of immunity of an animal and suppressed the skin reaction with a mechanism that may be either immunological or anti-inflammatory. It should be noted that the half life of GK is such that 24 hours after injection, i.e. at the time of antigen administration for either immunization or challenge, none of the injected GK is present in the animal. Thus, GK probably acted indirectly, via the mediation of some products of its enzymatic action.

FIG. 8 shows the results of an experiment in the collagen arthritis (CA) model in rats. A single injection of GK given at the time when the arthritic reaction begins to flare up induced an almost complete suppression lasting 4–5 days followed by the return to an almost unmodified arthritic reaction. On the other hand, repeated injections maintained suppression for the entire duration of the experiment. Thus, this experiment confirmed that the effects of GK in immune animals are short lived and do not reduce the state of immunity of the animals.

The effects described up to this point refer to in vitro phenomena or to the subcutaneous administration of GK. The fact that GK is found in high concentration in salivary glands and is secreted in saliva suggests that a significant physiological function of GK may occur via external salivary secretion. For this reason, we also tested the effects of orally administered GK in rats. Experiments of this nature were carried out in rats using the collagen arthritis model. This involves the injection of Type II collagen in an oil based adjuvant which induces an arthritic reaction beginning two weeks after immunization and lasting for the next 3–4 weeks. The variables we tested included the effects of a pre-treatment with oral collagen to induce tolerance to the subsequent immunization, the effects of the surgical removal of the submandibular gland and those of oral GK, given before tolerization and/or before immunization to normal and, sialoadenectomized (SMGx) rats. FIG. 2 demonstrates the results of one of such experiments. The oral pre-treatment with Type II collagen significantly reduced the arthritic response in normal rats but did not have such effect in SMGx animals. On the other hand, the oral administration of GK significantly reduced the arthritic reaction. FIG. 8 shows the results of another experiment which confirmed that sialoadenectomy interferes with tolerance induction. Moreover, this experiment demonstrated that the oral administration of GK to SMGx rats restores the ability of the mucosal immune system of these animals to develop tolerance upon oral collagen administration.

These results point to similarities and differences in the action of GK depending on whether it is used in vitro or in vivo and whether it is injected or given orally. The in vitro effects consisted of the stimulation of lymphocyte proliferation, while the in vivo effects appeared to be immunosuppressive. This apparent discrepancy may be explained if the in vivo effects, rather than true suppression, represented some form of immune deviation involving the reduction of the responses under investigation and the stimulation of other responses, not studied by us. The most likely mechanism for such an immune deviation would be a decrease of $T_{H1}$ activity and increase of $T_{H3}$ suppressor/regulatory T cell action. The responses we found to be suppressed by GK treatment were cell-mediated immunity (DTH, allograft rejection and CA) or T-dependent IgM production (direct PFC response). These responses would be suppressed by any mechanisms that reduce $T_{H}$ activity or favor the switch from IgM to any other immunoglobulin class. This explanation would be consistent with the fact that oral GK favors the induction of oral tolerance. This reaction is thought to involve a deviation from cell-mediated responses to IgA production induced by increased activity of TGF-beta producing $T_{H3}$ cells. Alternately suppressor cells may be activated by GK. Yet another possible explanation for the apparent discrepancy of in vitro versus in vivo effects would suggest that in vitro stimulation of lymphocyte proliferation was due to the formation of stimulatory peptides, formed by the action of GK on some substrate(s) contained in the culture system. Under in vivo conditions, the proteolytic action of GK result in the generation of suppressor/regulatory $T_{H3}$ lymphocytes. It is likely that the in vitro proliferative response reflects the expansion of these regulatory cells.

Differences in GK action were also observed when the route of GK administration was changed from subcutaneous to oral. In both situations, some suppression of immune reactions was observed if the treatment was simultaneous or shortly preceded antigen administration. On the other hand, the oral administration of GK appeared to enhance the induction of tolerance if given together with an oral antigen. The ensuing suppression of the arthritic reaction exceeded in duration and in magnitude the "immunosuppressive" effect of GK alone administered either by injection or by mouth. The same experiments also demonstrated that oral tolerance could not be induced by antigen alone in sialoadenectomized animals. Oral tolerance is a state of antigen specific hyporesponsiveness subsequent to the oral delivery of an antigen. It represents a protective reaction by the gut associated mucosal tissue (GALT) to prevent unnecessary and potentially harmful reactions to food antigens. It involves more than one mechanism. High antigen doses induce clonal deletion, while lower doses induce an active form of suppression or immune deviation, mediated by TGF-β producing T cells, referred to by some authors as $T_{H3}$ cells. The action of these cells suppresses $T_{H1}$ responses and favors $T_{H2}$ responses (114–116). From Peyer's patches, these regulatory cells migrate to periferal lymphoid organs and to all other tissues and organs, thus rendering systemic the immunosuppressive effect. Our results suggest that the SM gland plays a significant role in maintaining the normal responsiveness of GALT and that GK secretion in saliva is one of the factors involved in this function. The immunological effects of GK make this molecule an interesting candidate in the treatment of auotimmune diseases.

An immunosuppressive peptide of 40 kDa molecular weight, isolated from the submandibular glands (SMG*) of rats, had the capacity to suppress immune reactions upon parenteral administration to rats and mice. The peptide was identified as glandular kallikrein (K1) by partial sequencing and by enzymatic activity. Further experiments revealed that the excision of SMG (SMGx) from Lewis rats prevents the oral induction of immunological tolerance against native bovine type II collagen (BCII). Thus SMGx rats, when they were given oral BCII and were subsequently immunized with the same antigen, developed collagen induced arthritis (CA), while normal rats given an identical treatment were protected from the disease. When SMGx rats were orally given porcine K1 in conjunction with BCII, the capacity of such animals to develop oral tolerance was fully restored. These results indicate that normal SMG function is required for the induction of oral tolerance and that K1 is involved in mediating this function.

On the basis of current understanding of mucosal immunity and of the induction of immunological tolerance by the oral/nasal route this discovery will have relevance to the treatment of the following disease conditions: (i) autoimmune disease, for example, rheumatoid arthritis, multiple sclerosis, diabetes, myasthenia gravis, and the like. In these cases it is anticipated that the oral administration of K1 jointly with antigen would lead to the induction of tolerance, which in turn would cause the amelioration of symptoms; (ii) Inflammatory conditions, for example, colitis, connective tissue diseases and the like, in which a similar strategy may be feasible if the antigen/irritant is known; (iii) gene therapy; (iv) finally it is possible that the effectiveness of oral vaccination could be increased by the simultaneous oral administration of K1 inhibitors.

In one embodiment, there is provided a new approach for the amplification of orally induced immunological tolerance in patients suffering from rheumatoid arthritis. This new treatment involves the joint oral application of antigen and K1 of animal (eg. porcine) or human origin to patients. It is anticipated that K1 will increase the efficiency of oral tolerization with antigen, so that a new protocol for therapy could be developed.

The submandibular gland of laboratory rodents has been known to be an endocrine organ for a long time. It is also integrated into the immunoregulatory network. Immunoregulatory cytokines, such as TGF-β and immunoregulatory hormones, including nerve growth factor, epidermal growth factor, are produced in significant quantities by the SMG (1). We have identified glandular kallikrein as a powerful immunosuppressive principle in rat SMG (2–5), as outlined below.

The experimental evidence obtained in our laboratories is the following:

1) Semi-purified extracts of the SMG exert a suppressive effect on the antibody response, on contact sensitivity reactions, allograft rejection and on adjuvant-induced arthritis (2–5).

2) The active principle capable of mediating these effects was purified from rat SMG to homogeneity and shown to be a 40 kDa protein that was partially sequenced and found to be identical with glandular kallikrein (rK1).

3) The 40 kDa rK1 had the characteristic esterase activity of K1. The in vitro effects on lymphocyte proliferation and the in vivo immunosuppressive activities of rK1 were dependent on preserving its enzymatic activity.

4) Parenteral rK1 and porcine (p) K1 suppressed the contact sensitivity reaction to picryl chloride in mice. This suppression was inhibited when the animals were treated with the specific enzyme inhibitor, aprotinin in addition to K1 (FIG. 1).

5) We also demonstrated that the surgical removal of the submandibular gland (SMGx) in Sprague Dawley rats decreased the severity of collagen-induced arthritis (CA) and prevented the induction of oral tolerance in animals fed with native type II bovine collagen. Moreover, treatment of Sprague Dawley rats s.c. with rK1 after immunization with BCII suppressed the development of arthritis (FIG. 2) These results suggest that the SMG exerts both a stimulatory and suppressive effect on the autoimmune process.

6) In the collagen-induced arthritis model in Lewis rats, type II bovine collagen (BCII) in oil, given intradermally induced an arthritic reaction, which reached its maximum 4–5 weeks later. In this model, the oral administration of BCII (3 μg/day) prior to the induction on days −7, −5 and −3, suppressed the development of arthritis. If the submandibular gland was removed, the rats could not be tolerized in this manner. On the other hand, the oral administration of pK1 (100 IU/day) given on days −8, −5, and −3, fully restored the oral induction of immunological tolerance. The animals so treated were thus protected against the induction of arthritis by the subsequent challenge with BCII (FIG. 3, Table 1).

Taken together, these experimental results indicate that:

a) K1 is a powerful immunosuppressive agent, which is capable of exerting a systemic effect when given orally or parenterally;

b) Collagen induced arthritis in rats can be treated by the parenteral administration of rK1;

c) Salivary function is necessary for the induction of oral immunological tolerance to CA; and d) K1 restores the capacity to develop oral tolerance in animals with deficient salivary functions.

Two main hypotheses may be suggested to explain these results.

Hypothesis 1. K1 induces changes of immune responsiveness that include the suppression of ongoing immune responses and the facilitation of oral tolerance induction. These changes could be due to a direct action of K1 on immunocompetent cells or, more likely, may be mediated by the activation of biologically active molecules by the enzymatic action of K1. This effect could require doses higher than physiological and may not be related to any physiological function of salivary K1. The effect hypothesized here could be defined as a pharmacological one. According to this hypothesis, SMGx would produce alterations of the mucosal lymphoid tissue that may be due to mechanisms other than the loss of K1 secretion. In this case, the oral administration of K1 would overcome these effects in spite of the persisting deficiency of other salivary factors.

Hypothesis 2. Salivary K1 is a physiological regulator of mucosal immunity. According to this hypothesis, SMGx would deprive the animals of this essential factor and cause changes of the mucosal immune system that prevent oral tolerance induction. In this case, only the replacement of oral K1 would restore the normal balance in the mucosal lymphoid tissue.

The distinction of these two possibilities is important if one wants to predict the possible therapeutic applications of oral K1 and antigen in autoimmune conditions. In the first hypothesis, K1 would be expected to potentiate oral tolerance induction, irrespective of whether the salivary function is normal or not. In the second hypothesis, only patients with a deficient salivary secretion of K1 would benefit from the treatment.

Current evidence does not allow us to distinguish between these two possibilities. Results demonstrating a strong suppression of ongoing immune responses by parenteral application of K1 support the first hypothesis (FIG. 1.) (2). On the other hand, the more recent results with the oral administration of K1 jointly with BCII in SMGx rats appears to support the second hypothesis, while still being compatible with the first one (FIGS. 2, 3). The two above hypotheses are not mutually exclusive. It would be totally consistent with our current evidence to suggest that K1 may have a physiological role in maintaining a normal mucosal immune function while also inducing pharmacological effects in doses larger than physiological. In this case, oral K1 therapy would be beneficial in autoimmune conditions irrespective of a normal or deficient salivary function in the patient.

Lewis rats showed an excessive activation of the kallikrein-kinin system during experimental autoimmune inflammatory disease, whereas in Buffalo rats, a self-limiting disease developed, which was associated with a decreased rate of kininogen cleavage (18). Transgenic mice over-expressing the rat kallikrein binding protein (RKBP) showed elevated resistance to the lethal effect of endotoxin (19). The expression of human tissue kallikrein genes in mice had a profound effect on the histological structure of lymphoid tissue and led to a general decrease of lymphocytes, particularly in T-cell dependent areas (20). Immunoreactive K has been co-localized with prolactin in pituitary adenomas, where a role in processing of PRL to its 22 kDa form has been suggested. It has also been detected in normal pituitary tissue (9,21).

In general kallikreins are regarded as important local (autocrine-paracrine) regulators, that fine tune blood supply to inflamed tissues; stimulate the release of prolactin and growth hormone from the pituitary gland (which have a pro-inflammatory effect); increase Cl and glucose transport; participate in the generation of pain sensation; release transmitters from neurons; and stimulate DNA synthesis and growth in at least some cells, such as osteoclasts and endometrial stromal cells (9).

(ii) Kallikrein in rheumatoid arthritis. K has been detected in synovial fluid from arthritic joints (22), bronchial lavage from asthmatics (23) and in nasal secretions of patients with rhinitis (24,25). The source of GK in these inflammatory conditions is thought to be nasal and pulmonary secretory glands and infiltrating neutrophils (26).

Several studies ranging from the 1960s to very recent ones have shown that a significant proportion of patients suffering from rheumatoid arthritis (RA) have deficient salivary secretion (27,30). This deficient secretion includes not only a relatively small number of RA patients with secondary Sjögren's Syndrome (SS) but also a larger group of patients with sicca syndrome who are not usually classified as having SS. The reported proportion of patients with deficient salivary output varies from 30% to about 65%, with most of the authors giving figures in the 40–50% range.

Unfortunately, most of the authors who have studied salivary kallikrein secretion in RA patients report salivary concentrations only and the total output has not been calculated (31,33). If one takes into account that flows are sometimes markedly reduced (up to 90% reduction—34), this may result in a significantly decreased K1 secretion even if it is present in the saliva at slightly increased concentrations.

Friberg et al., (35) found that the salivary concentration of K in 7 patients with SS and no steroid treatment was 808 +/−179 units/liter (U/L; mean +/−S.D.). Stimulated whole morning saliva output for these patients has been 0.35+/− 0.18 ml/minute. The total output of K for this group of patients is 0.283 U/min. In the second group of 7 SS patients treated with steroids the salivary concentration of K was 361+/−265 U/L and the secretion rate 0.32+/−0.29 ml/min. Total output: 0.116 U/min. K concentration in saliva of 9 normal individuals was 170+/−83 U/L and saliva secretion 1.77 ml/min. Total production of K in normal individuals was 0.301 U/min. It is evident from these results that the increased K concentration in the saliva of the first group of patients, coupled with a major reduction of saliva production resulted in near normal output. On the other hand, total K production of SS patients that were on steroids was 38% of normal—clearly deficient. The mean total output of all patients was 0.199 U/min, which amounts to 66% of control values. It is worth noting that the group receiving no steroids was mainly composed of primary SS patients (without RA), while the group receiving steroids consisted mainly of RA patients with secondary SS. Recent findings suggest that blocking autoantibodies to the acetylcholine receptor present in the serum of primary Sjogren's syndrome can cause secretary abnormalities (36). This could explain the elevated K in the saliva of such patients as fluid and electrolyte secretion by the major salivary glands is under cholinergic control, whereas protein secretion is regulated by sympathetic nerve fibers that originate in the superior cervical ganglion (1). In the absence of further data, it cannot be established whether the low GK output in the second group was solely due to the use of steroids or also to the presence of RA.

Matthews et al. (37) reported a significant reduction of salivary flow in a group of 20 RA patients compared with 20 controls. Parotid flow in RA patients was 0.086 ml/minute, versus 0.196 ml/min in the controls (p<0.002). Submandibular flow in the RA group was 0.114 ml/minute, versus 0.186 ml/min in the controls (not significant). Kallikrein concentrations were only, and non-significantly, reduced with average concentrations of 0.304 units/mg of protein for parotid saliva (versus 0.557 in the controls) and 0.308 units/ml in submandibular saliva (versus 0.463 in the controls). Protein concentrations were practically unchanged. From these data, one may conclude that total GK output was reduced in the RA group. This study reports only data for the entire group of patients. Thus, it probably underestimates the reduction that must have taken place in the subgroup of patients complaining of xerostomia (15 out 20 patients).

(ii) Oral immunological tolerance is a well known phenomenon (first described in 1912) that is currently receiving much attention as a means to treat autoimmune diseases (56). There appear to be mechanisms for this phenomenon depending on the dose of the antigen. High antigen doses induce deletion or anergy of specific clones of $T_{H1}$ and $T_{H2}$ cells, while low doses induce the emergence of $T_{H2}$ clones that produce IL 4 and IL 10 and of $T_{H3}$ clones that produce TGFβ. These, in turn, suppress responses mediated by $T_{H1}$ cells. Thus, high doses of antigen appear to induce a true state of tolerance, while the effects of low doses would be better described as immune deviation phenomena. The successes of oral tolerization in experimental animals suggested its use in human autoimmune diseases. Several clinical trials have been performed in autoimmune diseases (56). Of particular interest here are the results of four trials (57–61) in RA patients. Such results demonstrated that RA patients receiving low doses of collagen showed statistically significant improvements. However, such improvements were not good enough for oral tolerance to become right now a commonly practiced therapy in RA. Some of the possible ways considered by various authors (60, 63) to improve the effectiveness of oral tolerance are: (i) better selection of patients; (ii) better selection of doses; and (iii) the use of additional treatment with adjuvants in order to potentiate tolerance.

As will be well known by one of skill in the art, gene therapy involves the insertion of non-host DNA into host cells, typically by viral vectors. A fundamental aspect of this technology is that the host must be tolerant to the virus used. Thus, another potential use of the above-described glandular kallikrein preparations would be to induce tolerance to viral vectors for gene therapy by administering the glandular kallikrein as described above when administering a viral vector for gene therapy using means known in the art. It is of note that this method would be suitable to induce such tolerance, which is a potentially important application.

As discussed above, described herein are methods of inducing tolerance to "foreign" material by administering glandular kallikrein as a method of treating or ameliorating for example autoimmune diseases. Specifically, as discussed above, the glandular kallikrein preparations are used to induce tolerance to the "foreign" material. It is of note that depletion of K1 will in fact decrease tolerance and in turn favours immunization, meaning that depletion of glandular kallikrein could be used for the potentiation of oral vaccines. Here it is envisioned, that the oral administration of an K1 inhibitor, for example, aprotinin in an amount effective to inhibit or reduce the activity of the glandular kallikrein with the antigen would be required to achieve an adjuvant effect.

While the preferred embodiments of the invention have been described above, it will be recognized and understood that various modifications may be made therein, and the appended claims are intended to cover all such modifications which may fall within the spirit and scope of the invention.

REFERENCES

1. E. Sabbadini and I. Berczi The submandibular gland: a key organ in the neuroimmunoregulatory network? (Review) Neuroimmunomodulation, 2(4):1 84–202, 1995
2. E. Nagy, I. Berczi, E. Sabbadini. Immunoregulatory effects of glandular kallikrein from the salivary submandibular gland of rats. Neuroimmunomodulation 4(2):107–112, 1997.
3. Kemp A., Mellow, L., and Sabbadini, E., Suppression and enhancement of in vitro lymphocyte reactivity by factors in rat submandibular gland extracts. Immunology 56: 261, 1985.
4. Kemp, A., Mellow, L., and Sabbadini, E., Inhibition of interleukin 1 activity by a factor in submandibular glands of rats. J. Immunol. 137: 2245, 1986.
5. Abdelhaleem, M. and Sabbadini, E. Identification of immunosuppressive fractions from the rat submandibular gland. Immunology 76:331, 1992.
6. Geterud, et al. (1991) Acta Otolaryng. 111:1153.
7. Kelly, S. M. et al. (1990) Brit. Med. J. 301:422.
8. Ridge-S C, et al., Type II collagen-induced arthritis in rats. Methods in Enzymology 162:355–373, 1988.
9. Clements J A. The human kallikrein gene family: a diversity of expression and frnction. Mol Cell Endocrinol. 99:C1–C6, 1994, 1994.
10. McCormack R T, Wang T J, Rittenhouse H G, Wolfert R L, Finlay J A, Lilja H, Sokoloff R L, Oesterling J E. Molecular forms of prostate-specific antigen and the human kallikrein gene family: A new era. Urology 45:729–744, 1995.
11. Takayama T K, Fujikawa K, Davie E W, Characterization of the precursor of prostate specific antigen. Activetioon by trypsin and by human glandular kallikrein. I. Biol Chem. 1997, 272:21582–8.
12. Naughton M A, Geczy C, Bender V, Hoffman H, Hamilton E: Biochim Biophys Acta 1972; 263:106–114.
13. Hu Z Q, Murakami K, Ikigai H, Shimamura T: Immunol Lett 1992; 32:85–90.
14. Perris A D, Whitfield J F: Proc Soc Exp Biol Med 1969; 130:1198–1201.
15. Ishizaka K: J Immunol 1985; 135:i–x
16. Verwaerde C, Auriault C, Neyrinck J L, Capron A: Scand J Immunol 1988; 27:17–24.
17. Matsushita S, Katz D H: Cell Immunol 1993; 146: 210–214.
18. Sartor A B, Cadena R E DeLa, Green K D, Stadnicki A, Davis S A, Schwaab J H, Adam A A, Raymond P, Coirnan R W. Selective kallikrein-kinin system activation in inbred rats susceptible to granulomatous enterocolitis. Gastroenterology, 110:1467–1481, 1996
19. Chen L-M, Chao L, Chao J. Beneficial effects of kallikrein-binding protein in transgenic mice during endotoxin shock. Life Sci 60:1431–1435, 1997.
20. Simson J A V, Wang J, Chao J, Chao L. Histopathology of lymphatic tissue in transgenic mice expressing human tissue kallikrein gene. Lab. Invest. 71:680–687, 1994.
21. Chao J, Chao, L. Functional analysis of human tissue kallikrein in transgenic mouse models. Hypertension, 27:491–494. 1998.
22. Worthy K, Bond P A, Elson C J, Dieppe P A, Bhoola K D. J Physiol. 425:66P, 1990.
23. Christiansen S C, Proud D, Cochrane C G. J Cin Invest 79:188–197, 1987.
24. Proud D, Togias A, Naclerio R M, Crush S B, Norman P S, Lichtenstein L M. J. Clin Invest 72:1678–185, 1983.
25. Baumgarten C R, Nichols R C, Naclerio R M, Proud D. J Immunol 137:1323–1328, 1986
26. Figueroa C D, Gonzalez C B, Muller-Esterl W, Bhoola K D. In Progress on Kinins (Fritz H, Jochum M, Muller-Esterl W, Roscher A, Luppertz K. eds) vol 38/I, pp. 617–626, Birkhauser-Verlag, Basel, 1992.
27. Ericson, S. et al. Acta Rheum. Scand. 1970; 16:60–80
28. Shearn, M. A. Sjögren Syndrome, in Major Problems in Internal Medicine vol II, 1971 W. B. Saunders Philadelphia; Sullivan, S. et al. Ann. Rheum. Dis. 1978; 37:164–7;
29. Russell, S. L. and Reisine, S. J. Am. Dent. Assoc. 1998; 129:733–9;
30. Jensen J. L. Ann. N. Y. Acad. Sci. 1998; 842:209–11.
31. Kerby, G. P. and Taylor, S. M. J. Lab. Clin. Invest. 1968; 71:704–8.
32. Hernandez C. C. et al. J. Rheumatol. 1998; 25:2381–4.
33. Greaves et al. Ann. Rheum. Dis. 1989; 48:753–9
34. Wang S L, Zhao Z T, Li J, Zhu X Z, Dong H, Zhang Y G. Arch. Investigation of the clinical value of total saliva flow rates. Arch. Oral Biol 1998; 43:39–43.

35. Friberg, B., Jonnsson, R. and Linde, A. Clin. Exp. Rheumatol. 1988; 6:135–8.
36. Robinson C P, Brayer J, Yamachika S, et al., Transfer of human serum antibodies to nonobese diabetic Igmu null mice reveals a role for autoantibodies in the loss of secretory function of exocrine tissues in Sjögren's syndrome. Proc. Nat. Acad. Sci, USA 1998, 95:7538–43.
37. Matthews et al., Ann. Rheum. Dis. 1985; 44: 20–6.
38. Roberts A B, Anzano M A, Lamb L C, Smith J M, Sporn M B: Proc Natl Acad Sci 1981; 78:5339–5343.
39. Wahl S M: J Clin Immunol 1992; 12:61–74.
40. Roberts A B, Sporn M B: Handbook of Pharmacology 95, 1990, pp 419–472.
41. Wahl S M, Hunt D A, Wakefield L, McCartney-Francis N, Wahl L M, Roberts A B, Sporn M B: Proc Natl Acad Sci 1987; 84:5788–5792.
42. Brandes M E, Mai V E H, Ohura K, Wahl S M: J Immunol 1991; 147:1600–1606.
43. Fava R A, Olsen N J, Postlethwaite A E, Broadley K N, Davidson J M, Nanney L B, Lucas C, Townes A S: J Exp Med 1991; 173:1121–1132.
44. Reibman J, Meisler S, Lec T C, Gold L I, Cronstein B N, Haines K A, Kolasinski S L, Weissman G W: Proc Natl Acad Sci 1991; 81:6805–6809.
45. Adams D H, Hathaway H, Shaw J, Burnett D, Elias E, Strain A J: J Immunol 1991; 147:609–612.
46. Allen J B, Manthey C L, Hand A, Ohura K, Ellingsworth L, Wahl S M: J Exp Med 1990; 171:231–247.
47. McCartney-Francis N, Wahl S M: J Leukocyte Biol 1994; 55:401–409.
48. Yamamura M, Uyemura K, Deans R J, Weinberg K, Rea T H, Bloom B R, Modlin R L. Science 1991; 254: 277–279.
49. Solgame P, Abrams J S, Clayberger C, Goldstein H, Convit Y, Modlin R L, Bloom B R: Science 1991; 254:279–282.
50. Lotz M, Kekow J, Carson D A: J Immunol 1990; 144:4189–4194.
51. Lee H M, Rich S: J Immunol 1991; 147:1127–1133.
52. Kehrl J H, Taylor A S, Delsing G A, Roberts A B, Sporn M B, Fauci A S: J Immunol 1989; 143:1868–1874.
53. Kehrl J H, Thevenin C, Rieckman P, Fauci A: J Immunol 1991; 146:4016–4023.
54. Sonoda E, Matsumoto R, Hitoshi Y, Ishii T, Sugimoto M, Araki S, Tominaga A, Yamaguchi N, Takatsu K: J Exp Med 1989; 170:1415.
55. Kim P H, Kagnoff M F: J Immunol 1990; 145:3773–3778.
56. Weiner, L. H. (997) Annu. Rev. Med. 48:341.
57. Trentham, D. E. et al. (1993) Science 261:1727.
58. Sieper, J. and Mitchison, A. N. (1994) Z. Rheumatol. 53:53.
59. Sieper J., (1996) Arthritis Rheum. 39:41.
60. Trentham, D. E., (1998) Rheum. Dis. Clin. N. A. 24:525. Barnett M L, Kremer J M, St.-Clair E W, et al., Treatment of rheumatoid arthritis with typeII collagen. Results of multicenetr, double-blind, placebo-controlled trial. Arthritis Rheum. 1998, 41:290–7.
61. Barnett M L, Kremer J M, St.-Clair E W, et al., Treatment of rheumatoid arthritis with typeII collagen. Results of multicenetr, double-blind, placebo-controlled trial. Arthritis Rheum. 1998, 41:290–7.
62. Gimsa U, Sieper J, Braun J, Mitchison N A, Type II collagen serology: a guide to clinical responsiveness to oral tolerance? Rheumatol. Int. 1997, 16:237–40
63. Kalden, J. R., and Sieper, J. (1998) Arthritis Rheum. 41: 191.
64. Kremer, J. M., Ed. (1998) Rheum. Dis. Clin. N. A. Vol. 24, No. 3.
65. Lin, F-K., Lin, C-H., Chou, C. C., Chen, K., Lu, H. S., Bacheller, W., Herrera, C., Jones, T., Chao, J. and Chao, L. Biophys. Biochem. Acta, 1993, 1173:325–28.
66. Angerman, A., Rahn, H.-P., Hektor, T., Fertig, G., Kemme, M. Eur. J. Biochem. 1992, 206:225–33.
67. Noble A, Kemeny D M. (1995) Immunology 85:357–363.
68. Shi F D, Clin Exp. (1998) Immunol. 111:506–512.
69. Knoerzer D B, et al. (1995), J Clin Invest 96:987–993.
70. I. Berczi, E. Nagy, S. L. Asa, K. Kovacs. The influence of pituitary hormones on adjuvant arthritis. Arthritis Rheum. 27:682–688 (1984).
71. Luna I G. Manual of Histologic Staining Methods of the Armed Forces Institute of Pathology. McGraw-Hill Inc., New York, pp 288, 1968.
72. Griffiths M M, et al. (1981) Arthritis Rheum 24:781–789.
73. Okumura S, McIntosh K, Drachman D B. Oral administration of acetylcholin receptor: Effects on experimental myasthenia gravis. Ann Neurol 36:704–713, 1994.
74. Edefrawi M E, Edefrawi A T. Purification and molecular properties of the acetylcholine receptor from *Torpedo electroplax*. Arch Biochem Biophys 159:363–373, 1973.
75. McIntosh K R, Drachman D B. Tolerance to acetylcholine receptor induced by AChR-coupled syngeneic cells. J Neuroimmunol 38:75–84, 1992.
76. Pestronk A, Drachman D B, Teoh R, Adams R N. Combined short-term immunotherapy cures experimental autoimmune myasthenia gravis. Ann. Neurol 14:235–241, 1983.
77. McIntosh K R, Drachman D B, Kuncl R W. Antigen-specific suppressor macrophages induced by culture with cyclosporin A plus acetylcholine receptor. J Neuroimmunol 25:75–89, 1989.
78. Lennon V A, Lindstrom J M, Seybold M E. Experimental autoimmune myasthenia: a model of myasthenia gravis in rats and guinea pigs. J Exp Med 141:1365–1375, 1975.
79. Ferreira H H A, Bevilacqua E, Gagioti S M, De Luca I M S, Zanardo R, Teixeira C E, Sannomiya P, Antunes E, De Nucci G. Nitric oxide modulates eosinophil infiltration in antigen-induced airway inflammation in rats. Eur J Pharmacol 358:253–259, 1998.
80. Morris G P, Beck P L, Herridge M S, Depew W T, Szewczuk M R, Wallace J L. Hapten-induced model of chronic inflammation and ulceration in the rat. Gastroenterology 96:795–803, 1989.
81. Ferretti M, Gionchetti P. Rizzello F, Venturi A, Stella P, Corti F, Mizrahi J, Miglioli M, Campieri M. Intracolonic release of nitric oxide during Trinitrobenzene sulphonic acid rat colitis. Digestive Dis Sci 42:2606–2611, 1997.
82. Neurath-M F, Fuss-I, Kelsall-B L, Presky-D H, Waegell-W, Strober-W. Experimental granulomatous colitis in 82. mice is abrogated by induction of TGF-β-mediated oral tolerance. J. Exp. Med. 183:2605–2616, 1996.
83. Tomasi M, Dertzbaugh M T, Hearn T, Hunter R L, Elson C O. Strong mucosal adjuvanticity of cholera toxin within lipid particles of a new multiple emulsion delivery system for oral immunization. Eur J Immunol. 27:2720–2725, 1997.
84. Söder, P. O., and Modeer T. Acta Odont. Scand. 1977; 35:41–50.
85. Jenzano, J. W., Coeffey, J. C., Heizer, W. D., Lundbard, R. L. Arch. Oral Biol. 1988, 33:641.
86. Dertzbaugh M T, Elson C O. Infect. Immun. 61:48, 1993
87. Felson-D T; et al. (1995) Arthritis-Rheum. 38(6): 727–35.
88. Sreebny L, Zhu W X Whole saliva and the diagnosis of Sjogren's syndrome: an evaluation of patients who complain of dry mouth and dry eyes. Part 2: Immunologic findings. Gerodontology. 1996; 13:44–8.
89. Uhlig T, Kvien T K, Jensen J L, Ax-Il T. Sicca symptoms, saliva and tear production, and disease variables in 636 patients with rheumatoid arthritis Ann Rheum Dis. 1999; 58:415–22.
90. Rhodus N, Dahmer L, Lindemann K, Rudney J, Mathur A, Bereuter sIgA and cytokine levels in whole saliva of Sjogren's syndrome patients before and after oral pilocarpine hydrochloride administration: a pilot study. J. Clin Oral Investig 1998; 2:191–4.
91. Larsen M J, Jensen A F, Madsen D M, Pearce E I. Individual variations of pH, buffer capacity and concentrations of calcium and phosphate in unstimulated whole saliva. Arch Oral Biol. 1999; 44:111–7.
92. Lenander-Lumikari M, Laurikainen K, Kuusisto P, Vilja P. Stimulated salivary flow rate and composition in asthmatic and non-asthmatic adults. Lenander-Lumikari M, Laurikainen K, Kuusisto P, Vilja P. Arch Oral Biol. 1998; 42:151–6.
93. Trautschold I: Assay methods in the kinin system; in Erdos E G (ed): Handbook of Experimental Pharmacology, Bradykinin, Kallidin and Kallikrein. Berlin, Springer, 1970, vol. 25, pp. 52–81.
94. Garrigue-Antar L, et aL, (1995) J. Immun. Method. 186:267–74.
95. Fries J F, Spitz P W, Young D Y. The dimensions of health outcomes: the health assessment questionnaire, disability and pain scales. J Rheumatol 1982; 9:789–93
96. Weinblatt M E, Coblyn J S, Fox D A, Fraser P A, Holdsworth D E, Glass D N, et al., Efficacy of low-dose methotrexate in rheumatoid arthritis. N. Engl. J. Med. 1985; 312:818–22.
97. Steinbrocker O, Traeger C H, Batterman R C. Therapeutic criteria in rheumatoid arthritis. JAMA 1949; 140: 659–62.
98. Fuller P J, Funder J W: The cellular physiology of glandular kallikrein. Kidney 1986; 29:953.
99. Wines D R, Brady J M, Pritchett D B, Roberts J L, MacDonald R J: Organization and expression of the rat kallikrein gene family. J Biol Chem 1989; 264:7653.
100. Bhoola K D, Figueroa C D, Worthy K: Bioregulation of kinins:kallikreins, kininogens, and kininases. Pharmacol Rev 1992; 44:1.
101. Alhenc-Gelas F, Marchetti J, Allegrini J, Corvol P, Menanrd J: Measurement of urinary kallikrein activity species differences in kinin production. Biochim Biophys Acta 1981; 677:477.
102. Simpson J A V, Chao J, and Chao L: Localization of kallikrein gene family proteases in rat tissues. Agents and Actions-Suppl. 1992; 38(Pt. 1):595.
103. Naughton M A, Geczy C, Bender V, Hoffman H, Hamilton E: Esteropeptidase and thymotopic activity of a protein isolated from the mouse submaxillary gland. Biochim Biophys Acta 1972; 263:106.
104. Hu Z Q, Murakami K, Ikigai H, Shimamura T: Enhancement of lymphocyte proliferation by mouse glandular kallikrein. Immunol Lett 1992; 32:85.
105. Perris A D, Whitfield J F: The mitogenic action of bradykinin on thymic lymphocytes and its dependence on calcium. Proc Soc Exp Biol Med 1969; 130:1198.
106. Ishizaka K: Twenty years with IgE: from the identification of IgE to regulatory factors for the IgE response. J Immunol 1985; 135:i–x.
107. Verwaerde C, Auriault C, Neyrinck J L, Capron A: Properties of serine proteases of Schistosoma mansoni. Shistosomula involved in the regulation of IgE synthesis. Scand J Immunol 1988; 27:17.
108. Matsushita S, Katz D H: Biphasic effect of kallikrein on IgE and IgG1 syntheses by LPS/IL4 stimulated B cells. Cell Immunol 1993; 146:210.
109. Kemp A, Mellow L, Sabbadini E: Suppression and enhancement of in vitro lymphocyte reactivity by factors in rat submandibular gland extracts. Immunology 1985; 56:261.
110. Abdelhaleem M, Sabbadini E: Identification of immunosuppressive fractions from the rat submandibular salivary gland. Immunology 1992; 76:331.
111. Nagy E, Berczi I, Sabbadini E: Immunoregulatory effects of glandular kallikrein from the salivary submandibular gland of rats. Neuroimmunomodulation 1997; 4:107.
112. Edman P, and Begg G: A protein sequenator. Eur. J. Biochem. 1967; 1:80.
113. Trautschold I: Assay methods in the kinin system. In Erdos G: Handbook of experimental pharmacology, Bradikinin, kallidin, and kallikrein. Berlin, Springer, 1970, vol. 25. p. 52–81.
114. Weiner H L, Friedman A, Miller A et al. Oral tolerance: immunologic mechanisms and treatment of animal and human organ-specific autoimmune diseases by dral administration of autoantigens. Annu. Rev. Immunol. 1994; 12:809.
115. Weiner H L: Oral tolerance: immune mechanisms and treatment of autoimmune diseases. Immunol. Today 1997; 18:335.
116. Friedman A, Weiner H L: Induction of anergy or active suppression following oral tolerance is determined by antigen dosage. Proc. Natl. Acad. Sci. 1994; 91:6683.

TABLE 1

Functional disability in rats with arthritis.

| | \*Days after challenge | | | | | | | | | | |
|---|---|---|---|---|---|---|---|---|---|---|---|
| | 14 | 16 | 18 | 21 | *23 | 25 | 28 | 31 | 35 | 38 | 42 |
| 1. Immune | 0/4 | 0/4 | 0/4 | 0/4 | 2/3 | 2/3 | 2/3 | 2/3 | 2/3 | 2/3 | 2/3 |
| 2. Imm + Tol | 0/5 | 0/5 | 0/5 | 0/5 | 0/4 | 0/4 | 0/4 | 0/4 | 0/4 | 0/4 | 1/4 |
| 3. Imm + SMX | 0/5 | 0/5 | 0/5 | 0/5 | 1/4 | 2/4 | 2/4 | 2/4 | 2/4 | 2/4 | 2/4 |
| 4. Imm. + Tol + SMX | 0/5 | 0/5 | 0/5 | 0/5 | 1/4 | 2/4 | 2/4 | 2/4 | 3/4 | 2/4 | 2/4 |
| 5. Imm. + Tol + SMX + pK1 | 0/5 | 0/5 | 0/5 | 0/5 | 0/4 | 0/4 | 0/4 | 0/4 | 0/4 | 0/4 | 0/4 |

The animals with functional deficit and deformities in their paws/total number of animals in the grouparе are given.
*On day 23 one animal was killed from each group for histologic examination.

TABLE 2

Effects of high molecular weight (HMW) and low molecular weight (LMW) pools of gel filtration fractions in three in vivo immunological assays. Modified from Ref. 110.

| Exp. Model | Treatment[a] | Groups | Results ± SD[b] | Significance[c] |
|---|---|---|---|---|
| Skin transplantation CBA/2J to C57B1/6J | 10 daily doses Days 0 to 9 | PBS | 12.2 ± 0.37 | |
| | | HMW | 13.0 ± 0.44 | NS |
| | | LMW | 14.7 ± 0.76 | $p < 0.05$ |
| Direct PFC | 5 daily doses Days 1 to 3 | PBS | 237.0 ± 19.7 | |
| | | HMW | 193.0 ± 12.0 | NS |
| | | LMW | 119.6 ± 10.0 | $p < 0.05$ |
| DTH (A/J mice) | 2 daily doses Days 4 and 6 | PBS | 19.0 ± 0.70 | |
| | | HMW | 18.2 ± 0.49 | NS |
| | | LMW | 9.0 ± 1.00 | $p < 0.01$ |

[a]The animals received the subcutaneous injection of 200 µl of PBS or PBS containing either the HMW or the LMW fractions. The doses corresponded to one-half of a SM gland (0.965 mg or 0.53 mg, respectively) and to one gland in the other models (1.93 mg or 1.06 mg, respectively).
[b]skin transplantation results are expressed as mean survival time; PFC response is expressed as the number of IgM anti-SRBC PFC per one million splenocytes; DTH results are expressed as increases of ear thickness in 1/10 mm units 24 hours after challenge.
[c]Significance was determined by two-sample t-test, using the PBS-treated group as the control; NS, not significant.

TABLE 3

Effects of the intradermal injection of rGK given before or after immunization in the DTH model.

| | Test on day: b | |
|---|---|---|
| Treatment[a] | 7 | 14 |
| None | 18.4 ± 0.76 | 17.6 ± 0.92 |
| rGK, Day − 1 | 6.0 ± 1.2* | 7.6 ± 0.98* |
| rGK, Day + 6 | 4.4 ± 0.63* | 16.8 ± 1.12 |
| rGK, Day + 13 | 19.0 ± 1.24 | 5.6 ± 0.78* |

[a]A/J mice were immunized by the application of 0.1 ml of a 5% solution of picryl chloride in ethanol to the skin of the abdomen; the day of immunization is referred to as day 0; the animals a single dose of 60 µg of rGK in 200 µl of PBS on the days indicated.
b. Animals were tested with the application of a 1% solution of picryl chloride in olive oil on one ear. Results are expressed in terms of the increase if the challenged ear over the pre-challenge values using units equivalent to 1/10 mm.
*$p < 0.05$.

The invention claimed is:

1. A method of suppressing an immune reaction to type II collagen in a human afflicted with or exhibiting at least one clinical sign of rheumatoid arthritis, the method comprising:
   selecting a human afflicted with or exhibiting at least one clinical sign of rheumatoid arthritis;
   administering to the human about 10 to about 5,000 International Units of a glandular kallikrein; and
   suppressing the immune reaction to type II collagen.

2. The method of claim 1, further comprising administering type II collagen with the glandular kallikrein.

3. The method of claim 1, wherein the glandular kallikrein comprises kallikrein-1, a fragment of a kallikrein having serine protease activity, or a mixture thereof.

4. The method of claim 1, comprising administering about 100 to about 1000 IU of glandular kallikrein.

5. The method of claim 1, wherein the human is afflicted with or exhibiting at least one clinical sign of collagen induced arthritis.

6. A method of enhancing immune system tolerance to type II collagen in an human afflicted with or exhibiting at least one clinical sign of rheumatoid arthritis, the method comprising:
   selecting a human afflicted with or exhibiting at least one clinical sign of rheumatoid arthritis;
   administering to the human about 10 to about 5,000 International Units of a glandular kallikrein; and
   reducing the human's immune response to type II collagen.

7. The method of claim 6, further comprising administering type II collagen with the glandular kallikrein.

8. The method of claim 6, wherein the glandular kallikrein comprises kallikrein-1, a fragment of a kallikrein having serine protease activity, or a mixture thereof.

9. The method of claim 6, comprising administering about 100 to about 1000 IU of glandular kallikrein.

10. The method of claim 6, wherein the human is afflicted with or exhibiting at least one clinical sign of collagen induced arthritis.

11. A method of inducing type II collagen-specific hyporesponsiveness in an human afflicted with or exhibiting at least one clinical sign of rheumatoid arthritis, the method comprising:
   selecting a human afflicted with or exhibiting at least one clinical sign of rheumatoid arthritis;
   administering to the human type II collagen and about 10 to about 5,000 International Units of a glandular kallikrein; and
   reducing the human's immune response to type II collagen.

12. The method of claim 11, comprising co-administering type II collagen with the glandular kallikrein.

13. The method of claim 11, wherein the glandular kallikrein comprises kallikrein-1, a fragment of a kallikrein having same protease activity, or a mixture thereof.

14. The method of claim 11, comprising administering about 100 to about 1000 IU of glandular kallikrein.

15. The method of claim 11, wherein the human is afflicted with or exhibiting ax least one clinical sign of collagen induced arthritis.

* * * * *

SEQUENCE LISTING

```
<160> NUMBER OF SEQ ID NOS: 1

<210> SEQ ID NO 1
<211> LENGTH: 26
<212> TYPE: PRT
<213> ORGANISM: Rattus rattus
<220> FEATURE:
<221> NAME/KEY: UNSURE
<222> LOCATION: (7)
<223> OTHER INFORMATION: unidentified, destroyed during Edman
      degradation process, likely cysteine
<220> FEATURE:
<221> NAME/KEY: UNSURE
<222> LOCATION: (26)
<223> OTHER INFORMATION: unidentified, destroyed during Edman
      degradation process, likely cysteine

<400> SEQUENCE: 1

Val Val Gly Gly Tyr Asn Xaa Glu Met Asn Ser Gln Pro Trp Gln Val
  1               5                  10                  15

Ala Val Tyr Tyr Phe Gly Glu Tyr Leu Xaa
             20                  25
```